(12) United States Patent
Aljuri et al.

(10) Patent No.: US 11,065,470 B2
(45) Date of Patent: Jul. 20, 2021

(54) TISSUE SAMPLING AND CATHETER SELECTION CANCER TREATMENT METHODS

(71) Applicant: PROCEPT BioRobotics Corporation, Redwood Shores, CA (US)

(72) Inventors: Nikolai Aljuri, Hillsborough, CA (US); Rodney Perkins, Woodside, CA (US)

(73) Assignee: PROCEPT BioRobotics Corporation, Redwood City, CA (US)

(*) Notice: Subject to any disclaimer, the term of this patent is extended or adjusted under 35 U.S.C. 154(b) by 68 days.

(21) Appl. No.: 16/384,637

(22) Filed: Apr. 15, 2019

(65) Prior Publication Data

US 2019/0240505 A1    Aug. 8, 2019

Related U.S. Application Data

(60) Division of application No. 15/587,336, filed on May 4, 2017, now Pat. No. 10,369,380, which is a
(Continued)

(51) Int. Cl.
*A61N 5/10* (2006.01)
*A61B 17/3203* (2006.01)
(Continued)

(52) U.S. Cl.
CPC .......... *A61N 5/1015* (2013.01); *A61B 5/0071* (2013.01); *A61B 5/0084* (2013.01);
(Continued)

(58) Field of Classification Search
CPC .......... A61M 2205/3334; A61M 1/008; A61M 25/0017; A61M 2210/166;
(Continued)

(56) References Cited

U.S. PATENT DOCUMENTS 5,007,897 A    4/1991    Kalb
5,653,683 A    8/1997    D'Andrea
(Continued)

FOREIGN PATENT DOCUMENTS

JP    H09154949    6/1997
JP    H11505435    5/1999
(Continued)

OTHER PUBLICATIONS

A to Z List of Cancer Drugs—National Cancer Institute. Aug. 18, 2016. 25 pages.
(Continued)

*Primary Examiner* — Christine H Matthews
*Assistant Examiner* — Joshua Daryl D Lannu
(74) *Attorney, Agent, or Firm* — Fisherbroyles LLP; John Shimmick

(57) ABSTRACT

A catheter treatment apparatus comprises an elongate tubular member and an expandable support. The expandable support comprises a radioactive substance to treat cancerous tissue and is configured to expand from a narrow profile for insertion to a wide profile to engage and treat tissue remaining after resection. The expandable support can be sized to fit within a volume of removed tissue to place the radioactive substance in proximity to the capsule and remaining tissue, to spare the capsule and proximate nerves and vessels to treat tissue in proximity to the capsule. The elongate tubular member may comprise a channel such as a lumen to pass a bodily fluid such as urine when the expandable support engages the tissue to treat the patient for a plurality of days. The treatment apparatus can be used to resect and diagnose tissue concurrently. Based on the diagnosis, targeted segmental treatment may be given.

13 Claims, 32 Drawing Sheets

Related U.S. Application Data continuation of application No. 15/388,449, filed on Dec. 22, 2016, now Pat. No. 10,016,620, which is a continuation of application No. PCT/US2015/037521, filed on Jun. 24, 2015.

(60) Provisional application No. 62/046,274, filed on Sep. 5, 2014, provisional application No. 62/018,359, filed on Jun. 27, 2014, provisional application No. 62/016,589, filed on Jun. 24, 2014.

(51) Int. Cl.

| | |
|---|---|
| *A61B 5/00* | (2006.01) |
| *A61B 18/22* | (2006.01) |
| *A61B 18/12* | (2006.01) |
| *A61B 18/14* | (2006.01) |
| *A61B 5/06* | (2006.01) |
| *A61M 25/00* | (2006.01) |
| *A61B 10/02* | (2006.01) |
| *A61B 8/12* | (2006.01) |
| *G01N 33/574* | (2006.01) |
| *A61B 90/00* | (2016.01) |
| *A61M 25/10* | (2013.01) |
| *A61M 1/00* | (2006.01) |
| *A61B 8/08* | (2006.01) |
| *A61B 18/00* | (2006.01) |
| *A61B 17/00* | (2006.01) |
| *A61B 90/50* | (2016.01) |
| *A61B 18/16* | (2006.01) |
| *A61B 18/04* | (2006.01) |

(52) U.S. Cl.
CPC .............. *A61B 5/061* (2013.01); *A61B 8/085* (2013.01); *A61B 8/12* (2013.01); *A61B 10/02* (2013.01); *A61B 10/0241* (2013.01); *A61B 10/0283* (2013.01); *A61B 17/3203* (2013.01); *A61B 17/32037* (2013.01); *A61B 18/1206* (2013.01); *A61B 18/1492* (2013.01); *A61B 18/22* (2013.01); *A61B 90/06* (2016.02); *A61B 90/37* (2016.02); *A61M 1/008* (2013.01); *A61M 25/0017* (2013.01); *A61M 25/10182* (2013.11); *A61M 25/10185* (2013.11); *A61N 5/1007* (2013.01); *A61N 5/1027* (2013.01); *G01N 33/57434* (2013.01); *A61B 5/0073* (2013.01); *A61B 18/16* (2013.01); *A61B 2010/0225* (2013.01); *A61B 2017/00274* (2013.01); *A61B 2017/32032* (2013.01); *A61B 2018/0022* (2013.01); *A61B 2018/00547* (2013.01); *A61B 2018/00577* (2013.01); *A61B 2018/00595* (2013.01); *A61B 2018/00863* (2013.01); *A61B 2018/046* (2013.01); *A61B 2018/126* (2013.01); *A61B 2018/1253* (2013.01); *A61B 2090/067* (2016.02); *A61B 2090/378* (2016.02); *A61B 2090/508* (2016.02); *A61B 2217/005* (2013.01); *A61B 2217/007* (2013.01); *A61B 2218/002* (2013.01); *A61B 2218/007* (2013.01); *A61B 2505/05* (2013.01); *A61B 2562/0219* (2013.01); *A61M 2205/0216* (2013.01); *A61M 2205/3334* (2013.01); *A61M 2205/3344* (2013.01); *A61M 2210/166* (2013.01); *A61N 2005/1011* (2013.01); *A61N 2005/1021* (2013.01); *A61N 2005/1024* (2013.01); *A61N 2005/1025* (2013.01); *A61N 2005/1094* (2013.01)

(58) Field of Classification Search
CPC ...... A61M 25/10185; A61M 25/10182; A61M 2205/3344; A61M 2205/0216; A61N 2005/1021; A61N 5/1027; A61N 2005/1094; A61N 2005/1011; A61N 5/1015; A61N 5/1007; A61N 2005/1024; A61B 2018/00863; A61B 2010/0225; A61B 10/02; A61B 8/12; A61B 2218/002; A61B 2218/007; A61B 2505/05; A61B 2562/0219; A61B 2017/32032; A61B 17/3203; A61B 10/0241; A61B 5/0084; A61B 5/0071; A61B 90/37; A61B 2217/007; A61B 2217/005; A61B 5/0073; A61B 2018/126; A61B 2018/1253; A61B 2018/046; A61B 2018/00595; A61B 2018/00577; A61B 2018/00547; A61B 2018/0022; A61B 18/22; A61B 18/16; A61B 18/1492; A61B 18/1206; A61B 5/061; A61B 2090/067; A61B 90/06; G01N 33/57434

See application file for complete search history.

(56) References Cited

U.S. PATENT DOCUMENTS

| | | | |
|---|---|---|---|
| 5,749,914 A | 5/1998 | Janssen | |
| 5,782,742 A | 7/1998 | Crocker | |
| 5,840,008 A | 11/1998 | Klein | |
| 5,904,679 A | 5/1999 | Clayman | |
| 5,947,889 A | 9/1999 | Hehrlein | |
| 6,036,631 A | 3/2000 | McGrath | |
| 6,302,870 B1 | 10/2001 | Jacobsen | |
| 6,491,619 B1 | 12/2002 | Trauthen | |
| 6,517,533 B1 | 2/2003 | Swaminathan | |
| 6,517,534 B1 | 2/2003 | McGovern | |
| 6,602,243 B2 | 8/2003 | Noda | |
| 6,923,754 B2 | 8/2005 | Lubock | |
| 7,022,131 B1 | 4/2006 | Derowe | |
| 7,837,670 B2 | 11/2010 | Barath | |
| 7,862,496 B2 | 1/2011 | Hermann | |
| 8,287,442 B2 | 10/2012 | Quick | |
| 8,353,895 B2 | 1/2013 | Russo | |
| 9,067,063 B2 | 6/2015 | Chi Sing | |
| 9,232,959 B2 | 1/2016 | Aljuri | |
| 10,016,620 B2 | 7/2018 | Aljuri | |
| 10,183,175 B2 | 1/2019 | Aljuri | |
| 10,342,993 B2 | 7/2019 | Perkins | |
| 10,369,380 B2 | 8/2019 | Aljuri | |
| 2001/0056219 A1 | 12/2001 | Brauckman | |
| 2003/0013973 A1* | 1/2003 | Georgakoudi | A61B 5/1459 600/473 |
| 2004/0092807 A1* | 5/2004 | Breskin | A61B 6/4258 600/407 |
| 2006/0020199 A1 | 1/2006 | Stubbs | |
| 2006/0100475 A1 | 5/2006 | White | |
| 2006/0217680 A1 | 9/2006 | Barath | |
| 2009/0227980 A1 | 9/2009 | Kangas | |
| 2009/0227998 A1* | 9/2009 | Aljuri | A61C 17/0202 606/13 |
| 2009/0312593 A1 | 12/2009 | Drobnik | |
| 2010/0094074 A1* | 4/2010 | Mark | A61M 25/10 600/3 |
| 2010/0100170 A1 | 4/2010 | Tan | |
| 2010/0173350 A1 | 7/2010 | Masilamani | |
| 2010/0222628 A1 | 9/2010 | White | |
| 2010/0280494 A1 | 11/2010 | Matsuura | |
| 2011/0152759 A1 | 6/2011 | Clymer | |
| 2011/0184391 A1 | 7/2011 | Aljuri | |
| 2011/0318339 A1* | 12/2011 | Smider | C07K 16/00 424/133.1 |
| 2013/0225902 A1 | 8/2013 | White | |
| 2014/0106986 A1* | 4/2014 | Knudsen | C12Q 1/6886 506/9 |

(56) References Cited

U.S. PATENT DOCUMENTS

| | | |
|---|---|---|
| 2014/0275715 A1 | 9/2014 | Brachman |
| 2015/0313666 A1 | 11/2015 | Aljuri |
| 2017/0231605 A1 | 8/2017 | Aljuri |
| 2017/0232228 A1 | 8/2017 | Aljuri |
| 2017/0232271 A1 | 8/2017 | Aljuri |
| 2017/0232272 A1 | 8/2017 | Perkins |
| 2017/0232273 A1 | 8/2017 | Aljuri |

FOREIGN PATENT DOCUMENTS

| | | |
|---|---|---|
| JP | 2000516831 | 12/2000 |
| JP | 2002136599 | 5/2002 |
| JP | 2002515773 | 5/2002 |
| JP | H11508798 | 6/2003 |
| JP | 2005505384 | 2/2005 |
| JP | 2006505346 | 2/2006 |
| JP | 2008178704 | 8/2008 |
| JP | 2009515603 | 4/2009 |
| JP | 2010500103 | 1/2010 |
| JP | 2013541401 | 11/2013 |
| WO | 9702794 | 1/1997 |
| WO | 03020106 A2 | 3/2003 |
| WO | 2007106530 | 9/2007 |
| WO | 2008083407 | 7/2008 |
| WO | 2009111736 | 9/2009 |
| WO | 2011097505 A1 | 8/2011 |
| WO | 2013006764 A1 | 1/2013 |
| WO | 2013010600 A1 | 1/2013 |
| WO | 2013130895 | 9/2013 |
| WO | 2013130895 A1 | 9/2013 |
| WO | 2014127242 | 8/2014 |
| WO | 2014131742 A1 | 9/2014 |
| WO | 2014165703 | 10/2014 |
| WO | 2015035249 A2 | 3/2015 |
| WO | 2015200538 | 12/2015 |
| WO | 2017174950 A1 | 10/2017 |

OTHER PUBLICATIONS

Brachytherapy—Wikipedia the free encyclopedia. Aug. 1, 2016. 12 pages.
CardinalHealth FDA approved list v10. Nov. 1, 2014. 12 pages.
Foley Catheter, Wikipedia, dated Jan. 30, 2013.
International Search Report dated Oct. 5, 2015 for International Application No. PCT/US2015/037521.
List of antibodies—Wikipedia the free encyclopedia. Aug. 10, 2016. 12 pages.
List of Pain Relief Medications—eMed Expert. Jan. 12, 2016. 5 pages.
List of Radiopharmaceuticals nuclearpharmacy. Jul. 20, 2015. 3 pages.
Parekh, et al., Assessment of 54 biomarkers for biopsy-detectable prostate cancer. Cancer Epidemiol Biomarkers Prev. Oct. 2007; 16(10):1966-72.
Radiopharmaceutical List and Package Inserts. University of Arkansas for Medical Sciences, Jan. 12, 2016. 4 pages.

\* cited by examiner

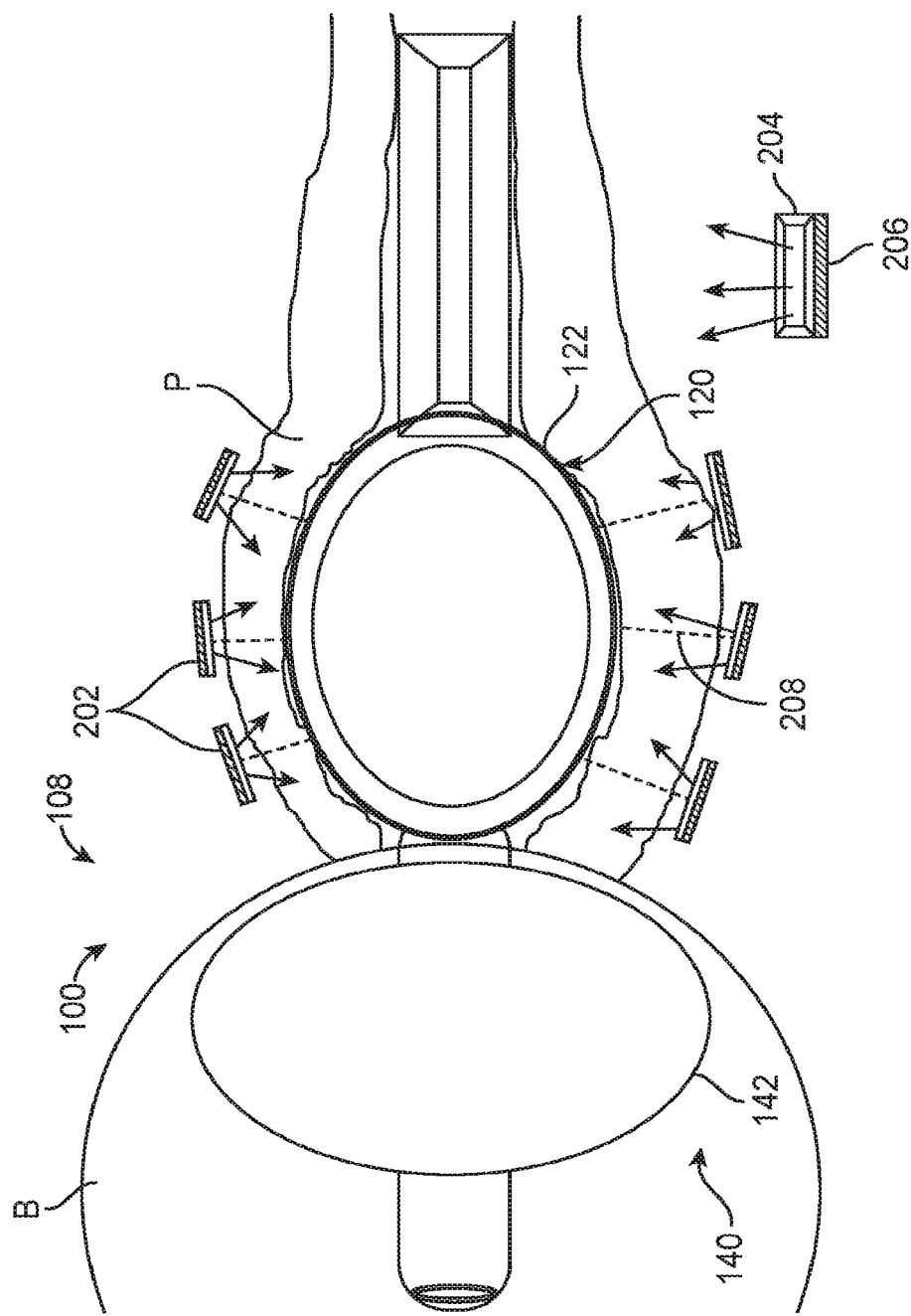
FIG. 17A1

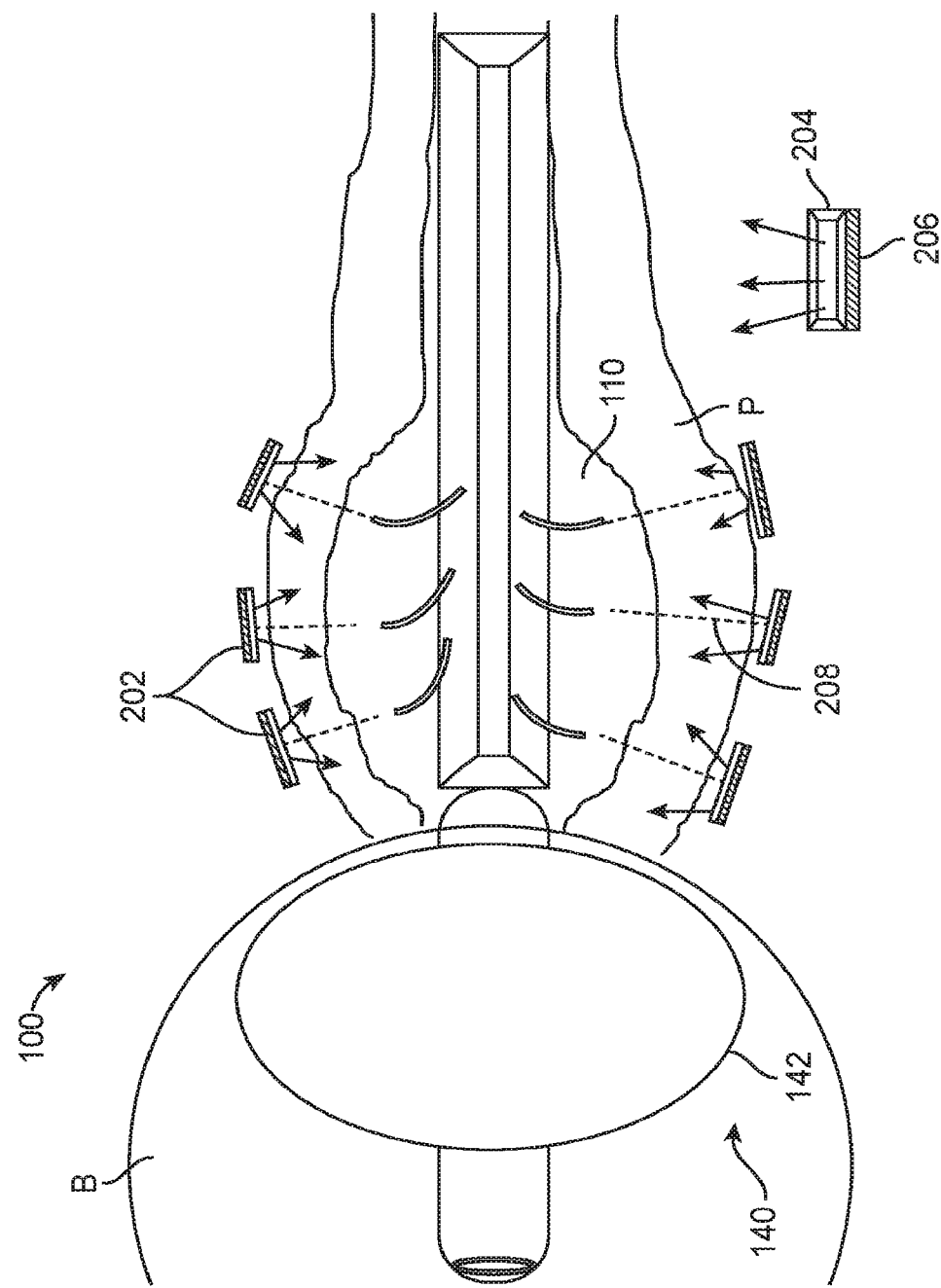
FIG. 17A2

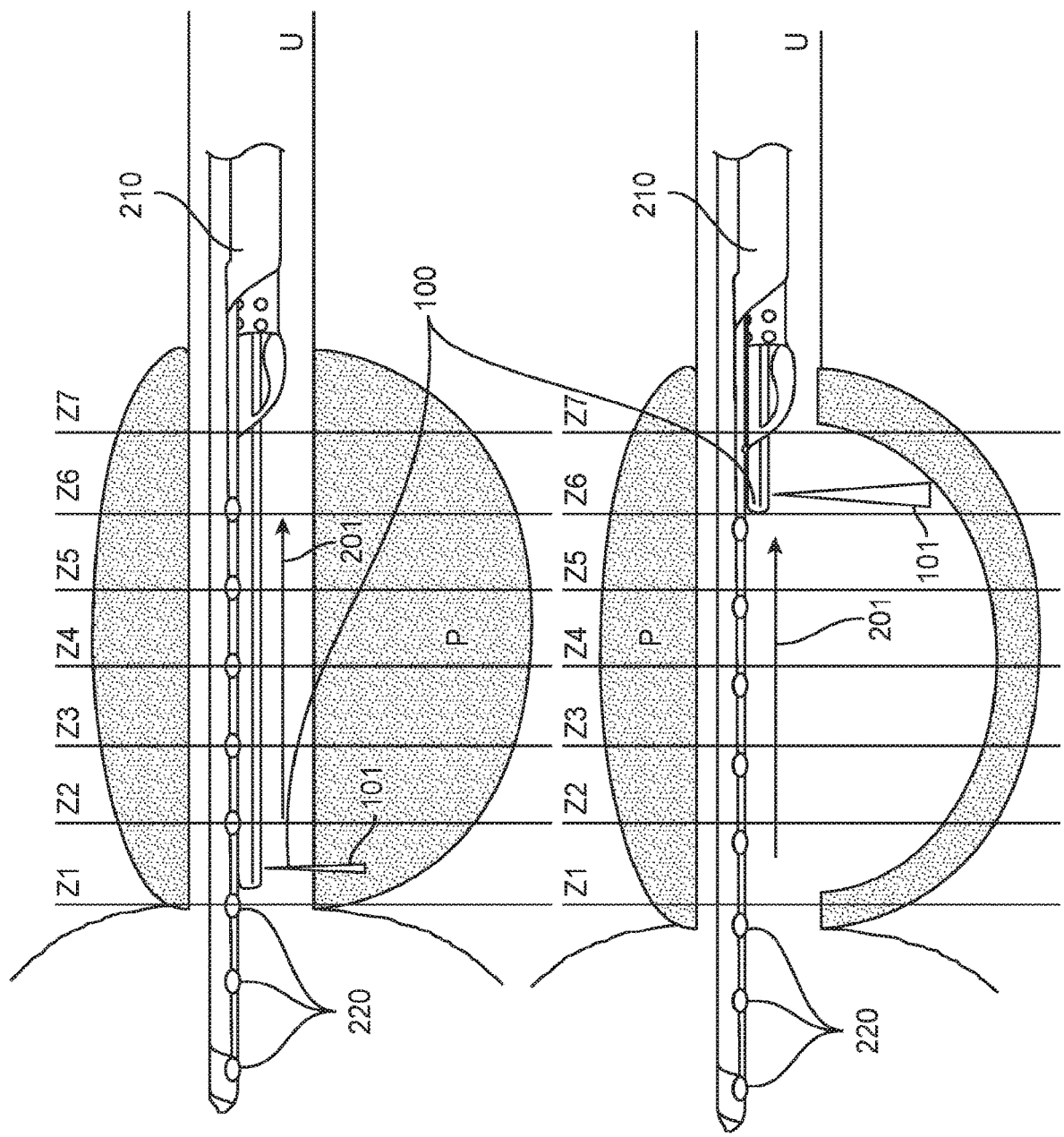

TISSUE SAMPLING AND CATHETER SELECTION CANCER TREATMENT METHODS

RELATED APPLICATIONS

The present application is a divisional application of U.S. patent application Ser. No. 15/587,336, filed May 4, 2017, now U.S. Pat. No. 10,369,380, issued Aug. 6, 2019, which is a continuation of U.S. patent application Ser. No. 15/388,449, filed on Dec. 22, 2016, now U.S. Pat. No. 10,016,620, issued Jul. 10, 2018, which is a bypass continuation of International Application No. PCT/US2015/037,521, filed Jun. 24, 2015, which claims priority to U.S. Provisional Patent Application No. 62/016,589, filed Jun. 24, 2014, to U.S. Provisional Patent Application No. 62/018,359, filed Jun. 27, 2014, and to U.S. Provisional Patent Application No. 62/046,274, filed Sep. 5, 2014, the entire disclosures of which are incorporated herein by reference.

The subject matter of this PCT application is related to and incorporates by references the complete disclosures of the following commonly owned U.S. patents and applications: U.S. application Ser. No. 12/700,568, filed Feb. 4, 2010, now U.S. Pat. No. 9,232,959, issued Jan. 12, 2016, U.S. Provisional Application No. 61/874,849, filed Sep. 6, 2014, U.S. Provisional Application No. 61/972,730, filed Mar. 31, 2014, and U.S. Provisional Application No. 62/019,305, filed Jun. 30, 2014.

The subject matter of this PCT application is also related to International Application No. PCT/US2013/028,441, filed 28 Feb. 2013, published as WO2013130895 on Sep. 6, 2013, and to International Application No. PCT/US2011/023,781, filed on Feb. 4, 2011, published as WO2011097505 on Nov. 8, 2011, the full disclosure of which is incorporated herein by reference.

BACKGROUND

The field of the present invention is related to tissue sample and the treatment of cancer tissue, and more specifically to the tissue sampling and treatment of an organ such as the prostate.

Prior methods and apparatus of treating subjects such as patients can result in less than ideal results in at least some instances. For example, prior methods of prostate surgery can result in longer healing time and less than ideal outcomes in at least some instances.

Many organs such as the prostate comprise an outer wall or capsule, which comprises sensitive nerves or blood vessels. Damage to the nerves or vessels can lead to decreased functioning of the organ, and the prior methods and apparatus can provide less than ideal removal of tissue near capsules and walls of organs. For example, damage to nerves of the prostate capsule may lead to decreased potency, and damage to the optic nerve or vessels of the eye can lead to decreased vision in at least some instances.

Also, the prior methods and apparatus for sampling of tissue to collect cells may result in less ideal results in at least some instances.

In light of the above, it would be helpful to provide improved methods and apparatus for surgery and treating cancer. Ideally such methods would provide improved treatment near delicate tissue structures such as nerves and vessels of the organ with improved outcomes.

The field of the present invention is related to the sampling of cells and tissue and treatment of tissue, and more specifically to the sampling and treatment of an organ such as the prostate.

Although early diagnosis and treatment of cancer can provide improved outcomes, the prior methods and apparatus of diagnosing and treating cancer can be less than ideal. In at least some instances, patients having benign prostate hyperplasia (BPH) may also have prostate cancer (PCa), which may not be diagnosed as quickly as would be ideal. Also, the prior methods and apparatus for treating cancer may be less than ideally suited for combination with other treatments, for example.

In light of the above, it would be helpful to provide improved methods and apparatus for surgery and diagnosing and treating cancer. Ideally such methods would provide improved treatment of delicate tissue structures such as nerves and vessels of the organ, and determine the presence or absence of cancer and provide improved treatments with improved outcomes.

SUMMARY

Embodiments of the present invention provide improved methods and apparatus for the treatment of patients who may be at risk for cancer, and are well suited for combination with surgical treatments such as tissue resection. The resected tissue may comprise hyperplasia of an organ having a capsule such as the prostate, in which delicate vessels and nerves are located proximate the capsule. The embodiments disclosed herein can treat tissue near the capsule with decreased damage to the capsule and adjacent tissue structures such as blood vessels and nerves. In many embodiments, a catheter treatment apparatus comprises an elongate tubular member and an expandable support sized together to place the expandable support in the treated organ. In many embodiments, the expandable support comprises a radioactive substance to treat cancerous tissue, and the expandable support is configured to expand from a narrow profile configuration for insertion to a wide profile configuration to in order to engage and treat tissue remaining after resection. The expandable support can be sized to fit within a volume of removed tissue in order to place the radioactive substance in proximity to the capsule and remaining tissue, in order to spare the capsule and proximate nerves and vessels in order treat tissue in proximity to the capsule. The elongate tubular member may comprise a channel such as a lumen to pass a bodily fluid such as urine when the expandable support engages the tissue in order to treat the patient for a plurality of days. In many embodiments, a second catheter without a radioactive substance is provided to the physician, and the patient treated with the catheter having the radioactive substance or the second catheter without the radioactive substance.

The expandable support can be configured in one or more of many ways to position the support in proximity to the remaining tissue, and may comprise a balloon, or a plurality of expandable struts, and combinations thereof. The elongate tubular member may comprise a plurality of internal channels, such as a first lumen and a second lumen, in which the first lumen comprises a longitudinal length and cross-sectional width in order to allow passage of the bodily fluid, and the second lumen comprises a longitudinal length and a cross-sectional width in order to fill the balloon. In many embodiments, the expandable support is configured to retract to a narrow profile configuration for removal when the support has been placed for a plurality of days.

The radioactive substance can be placed on the support in one or more of many ways in order to treat the tissue, and may comprise one or more of seeds, barbs, a fluid, or a layer of radioactive material. In many embodiments, the radioactive substance comprises a plurality of radioactive seeds placed at a plurality of locations on the expandable support. The radioactive seeds may be located in pockets of the support in order to retract with the support for removal with the support. The radioactive seeds may comprise a size and number sufficient to deliver a dosage of radiation to the patient with a radiation treatment profile when placed for a plurality of days, and the seeds can be spaced apart on the support with the expanded profile configuration in order to provide the radiation treatment profile when the support comprises the expanded profile configuration. In many embodiments, the seeds are spaced apart on the support with substantially uniform distances over at least a portion of the support in order to provide a substantially uniform treatment profile. The placement of the seeds in proximity to the capsule can allow for treatment of hyperplasia near the capsule without penetrating the capsule. Alternatively, the radioactive substance may comprise a plurality of barbs released from the support when the support expands for implantation in the patient, and the barbs can be sized to avoid penetration of the capsule or to penetrate the capsule as appropriate. In many embodiments, the physician is provided with a plurality of three catheters, and one of the catheters inserted into the patient in response to testing of the resected tissue sample collected from the patient. Alternatively, a catheter without the radioactive material can be provided to the physician, and the physician can inject the radioactive substance, for example with filling of the balloon with the radioactive substance.

While embodiments of the present invention are specifically directed at transurethral treatment of the prostate, certain aspects of the invention may also be used to treat and modify other organs such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

Embodiments of the present invention provide improved methods and apparatus for the treatment of patients who may be at risk for cancer, and are well suited for combination with surgical treatments such as tissue resection. The resected tissue may comprise hyperplasia of an organ having a capsule such as the prostate, in which delicate vessels and nerves are located proximate the capsule. The embodiments disclosed herein can treat tissue near the capsule with decreased damage to the capsule and adjacent tissue structures such as blood vessels and nerves. In many embodiments, a catheter treatment apparatus comprises an elongate tubular member and an expandable support sized together to place the expandable support in the treated organ. In many embodiments, the expandable support comprises a radioactive substance to treat cancerous tissue, and the expandable support is configured to expand from a narrow profile configuration for insertion to a wide profile configuration to in order to engage and treat tissue remaining after resection. The expandable support can be sized to fit within a volume of removed tissue in order to place the radioactive substance in proximity to the capsule and remaining tissue, in order to spare the capsule and proximate nerves and vessels in order treat tissue in proximity to the capsule. The elongate tubular member may comprise a channel such as a lumen to pass a bodily fluid such as urine when the expandable support engages the tissue in order to treat the patient for a plurality of days. In many embodiments, a second catheter without a radioactive substance and a diagnostic test from a surgical tissue sample is provided to the physician, and the patient treated with the catheter having the radioactive substance or the second catheter without the radioactive substance in response to the diagnostic test.

The expandable support can be configured in one or more of many ways to position the support in proximity to the remaining tissue, and may comprise a balloon, or a plurality of expandable struts, and combinations thereof. The elongate tubular member may comprise a plurality of internal channels, such as a first lumen and a second lumen, in which the first lumen comprises a longitudinal length and cross-sectional width in order to allow passage of the bodily fluid, and the second lumen comprises a longitudinal length and a cross-sectional width in order to fill the balloon. In many embodiments, the expandable support is configured to retract to a narrow profile configuration for removal when the support has been placed for a plurality of days.

The radioactive substance can be placed on the support in one or more of many ways in order to treat the tissue, and may comprise one or more of seeds, barbs, a fluid, or a layer of radioactive material. In many embodiments, the radioactive substance comprises a plurality of radioactive seeds placed at a plurality of locations on the expandable support. The radioactive seeds may be located in pockets of the support in order to retract with the support for removal with the support. The radioactive seeds may comprise a size and number sufficient to deliver a dosage of radiation to the patient with a radiation treatment profile when placed for a plurality of days, and the seeds can be spaced apart on the support with the expanded profile configuration in order to provide the radiation treatment profile when the support comprises the expanded profile configuration. In many embodiments, the seeds are spaced apart on the support with substantially uniform distances over at least a portion of the support in order to provide a substantially uniform treatment profile. The placement of the seeds in proximity to the capsule can allow for treatment of hyperplasia near the capsule without penetrating the capsule. Alternatively, the radioactive substance may comprise a plurality of barbs released from the support when the support expands for implantation in the patient, and the barbs can be sized to avoid penetration of the capsule or to penetrate the capsule as appropriate. In many embodiments, the physician is provided with a plurality of three catheters, and one of the catheters inserted into the patient in response to testing of the resected tissue sample collected from the patient. Alternatively, a catheter without the radioactive material can be provided to the physician, and the physician can inject the radioactive substance, for example with filling of the balloon with the radioactive substance.

While embodiments of the present invention are specifically directed at transurethral treatment of the prostate, certain aspects of the invention may also be used to treat and modify other organs such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIGS. 17A1 and 17A2 show a treatment apparatus comprising radioactive pellets in accordance with many embodiments;

FIGS. 21A and 21B show sectional views of a treatment apparatus in use to treat a patient in accordance with many embodiments;

DETAILED DESCRIPTION

Figure 1:
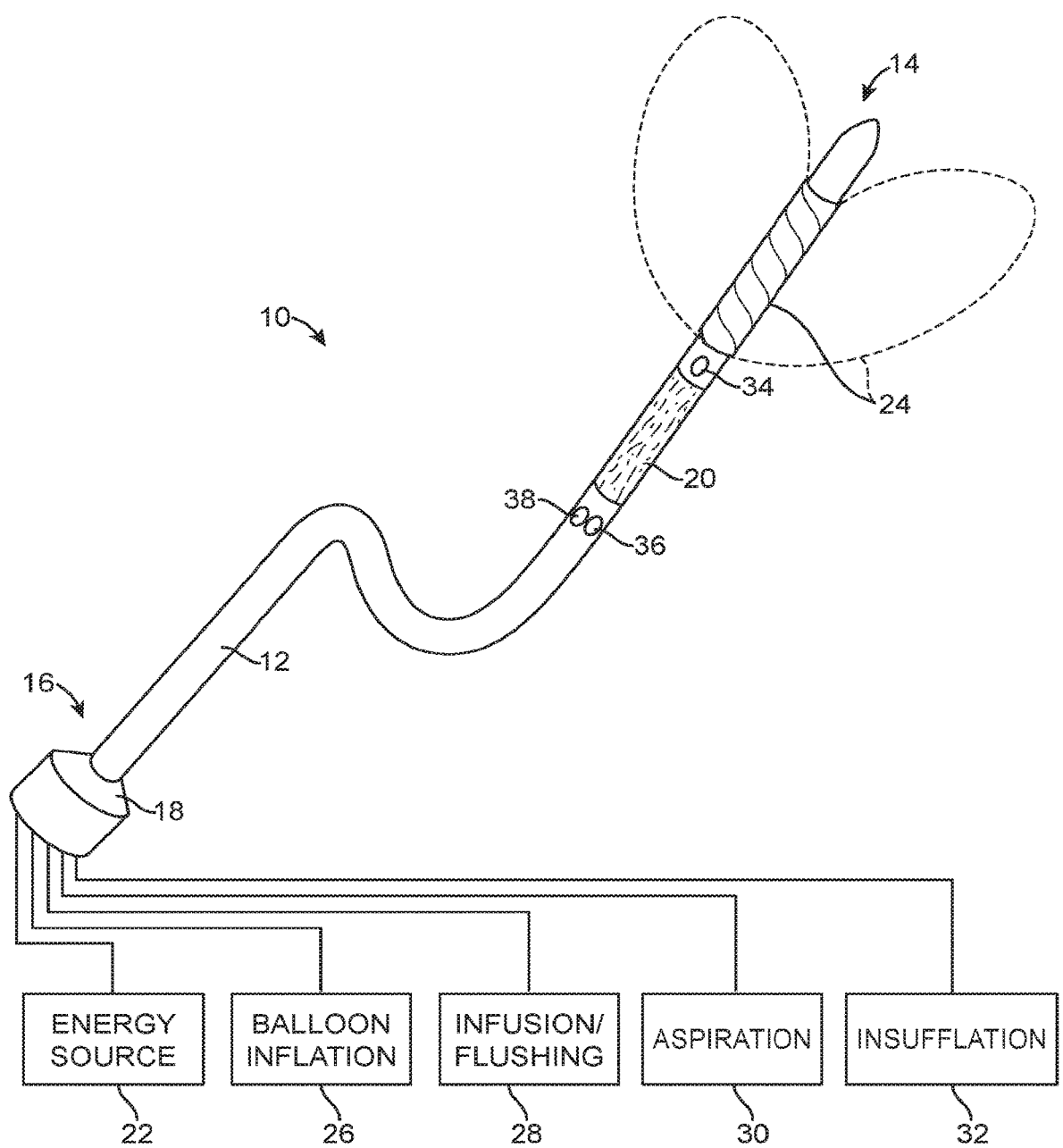
FIG. 1 is a schematic illustration of a device suitable for performing intraurethral prostatic tissue debulking in accordance with embodiments.

A better understanding of the features and advantages of the present disclosure will be obtained by reference to the following detailed description that sets forth illustrative embodiments, in which the principles of embodiments of the invention are utilized, and the accompanying drawings.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described herein.

The embodiments as disclosed herein can be used to collect fat cells and prostate tissue, and many other tissue types of tissue, such as tissue from other organs, for example.

The embodiments disclosed herein can be combined in one or more of many ways to provide improved therapy to a patient. The disclosed embodiments can be combined with prior methods and apparatus to provide improved treatment, such as combination with known methods of prostate surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments. Methods and apparatus of tissue removal suitable for incorporation in accordance with embodiments as disclosed herein are described in: PCT/US2013/028441, filed 28 Feb. 2013; U.S. Provisional Application No. 61/874,849, filed Sep. 6, 2014; U.S. Provisional Application No. 61/972,730, filed Mar. 31, 2014; the entire disclosures of which have been previously incorporated herein by reference.

Although the treatment planning and definition of treatment profiles and volumes as described herein are presented in the context of prostate surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, etc. as well as body lumens and passages such as the sinuses, ureter, colon, esophagus, lung passages, blood vessels and throat.

As used herein, A and/or B encompasses A alone, B alone, and combinations of A and B together.

As used herein, the term Aquablation™ encompasses ablation with water.

As used herein, the words telescope, endoscope and cytoscope are used interchangeably.

As used herein, the terms entrainment region and cavitation region are used interchangeably.

As used herein, a non-radioactive substance encompasses a substance which may have trace amounts of background radiation but which does not have enough radiation to provide a treatment.

The imaging and treatment probes as described herein can be combined in one or more of many ways, and in many embodiments the images of the patient can be used to define a target volume and a target profile of the volume of tissue removed. The profile of tissue removed can be planned to efficaciously remove tissue. The methods and apparatus for imaging as described herein can be used to beneficially plan for treatment. Alternatively or in combination, the imaging methods and apparatus as described herein can be used to modify the treatment in real time as the patient is treated, for example.

The visible entrainment and cavitation region can be combined with the images of tissue and treatment regions shown on the display, so as to provide confirmation that the correct amount of tissue will be resected. In many embodiments, the distance of the visible entrainment region corresponds to a maximum cut depth, such that the surgeon can select the depth of the cut based on images and with adjustment of treatment parameters such as one or more of flow rate, nozzle diameter, or pressure.

The visible entrainment region as described herein comprises region of cavitation of the fluid stream emitted from the energy source such as a nozzle, and the maximum resection depth corresponds to the distance of the visible entrainment region. By visible entrainment region, it is meant that the user can visualize the entrainment region with imaging sensitive to formation of cavitation pockets, such as visible and ultrasound imaging which scatter waves in response to cavitation pockets being formed.

As used herein a processor encompasses one or more processors, for example a single processor, or a plurality of processors of a distributed processing system for example. A controller or processor as described herein generally comprises a tangible medium to store instructions to implement a steps of a process, and the processor may comprise one or more of a central processing unit, programmable array logic, gate array logic, or a field programmable gate array, for example.

As used herein like characters and numerals identify like elements.

As used herein, real-time a real time image shown on a display encompasses an image shown within a few seconds of the event shown. For example, real time imaging of a tissue structure encompasses providing the real time image on a display within about ten seconds of the image being acquired.

As used herein, the terms distal and proximal refer to locations referenced from the apparatus, and can be opposite of anatomical references. For example a distal location of a probe may correspond to a proximal location of an elongate member of the patient, and a proximal location of the probe may correspond to a distal location of the elongate member of the patient.

Automated robotic control—where movement of the water jet is motorized and under computer control with preselected routines—allows accurate and finely detailed resections not possible with manual control. Advantages include reduced time required for procedures, fewer complications, improved outcomes and less training time needed for surgeons. Many of these improvements arise from reducing or eliminating the need for manual dexterity of the treating physician. Automatic control further allows the cutting power of the nozzle to be increased to levels not achievable with full manual control. The system may be manually controlled during less critical portions of the procedure, e.g. during initial selection of an area to operate on and for touch-ups in cutting and cautery. Even during these less critical phases of the protocols, the increased precision and smoothness provided by the automated control can provide reduction and filtering of hand jitter. Another significant advantage is that automation allows for pretesting or "dry runs" of a procedure. When a cutting routine is selected, the limits of area can be selected using a joystick or other control element to position the laser during a mock the procedure without cutting. Changes can be made before cutting commences, so that errors can be corrected before beginning the actual procedure.

INCORPORATION BY REFERENCE

Figure 2A:
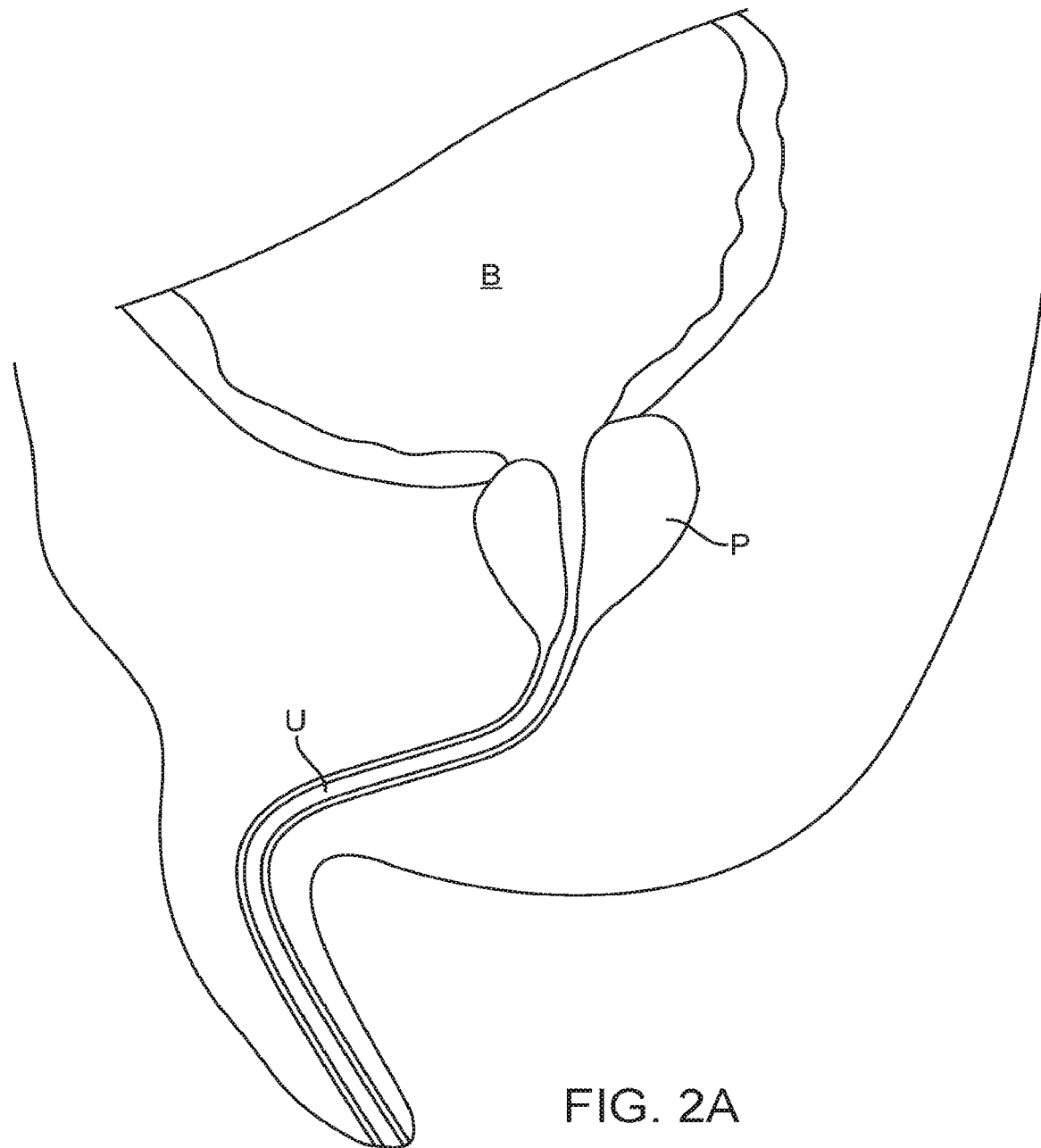
FIGS. 2A-2D illustrate use of the device of FIG. 1 in performing prostatic tissue debulking.
Figure 2B:
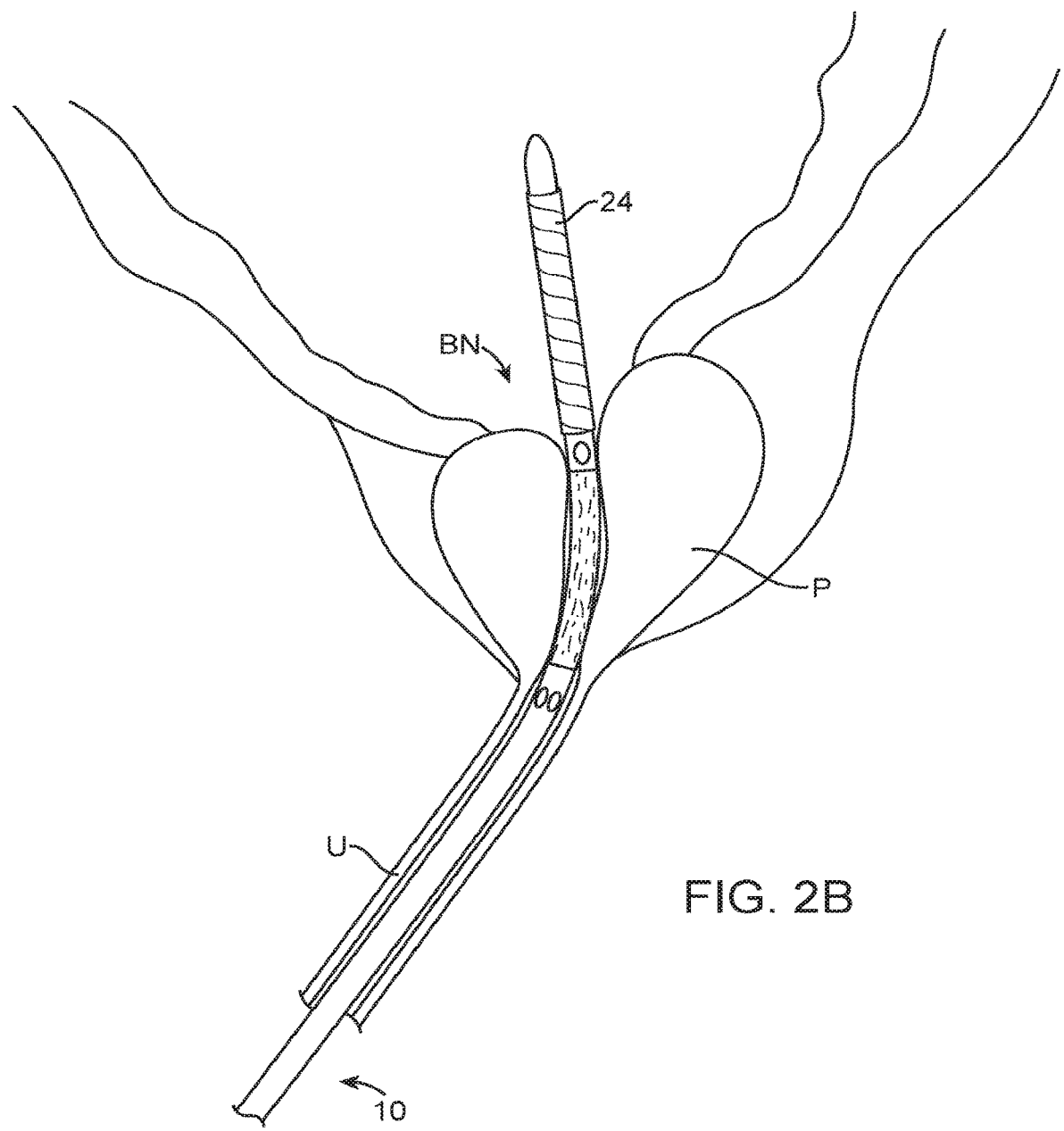
Figure 2C:
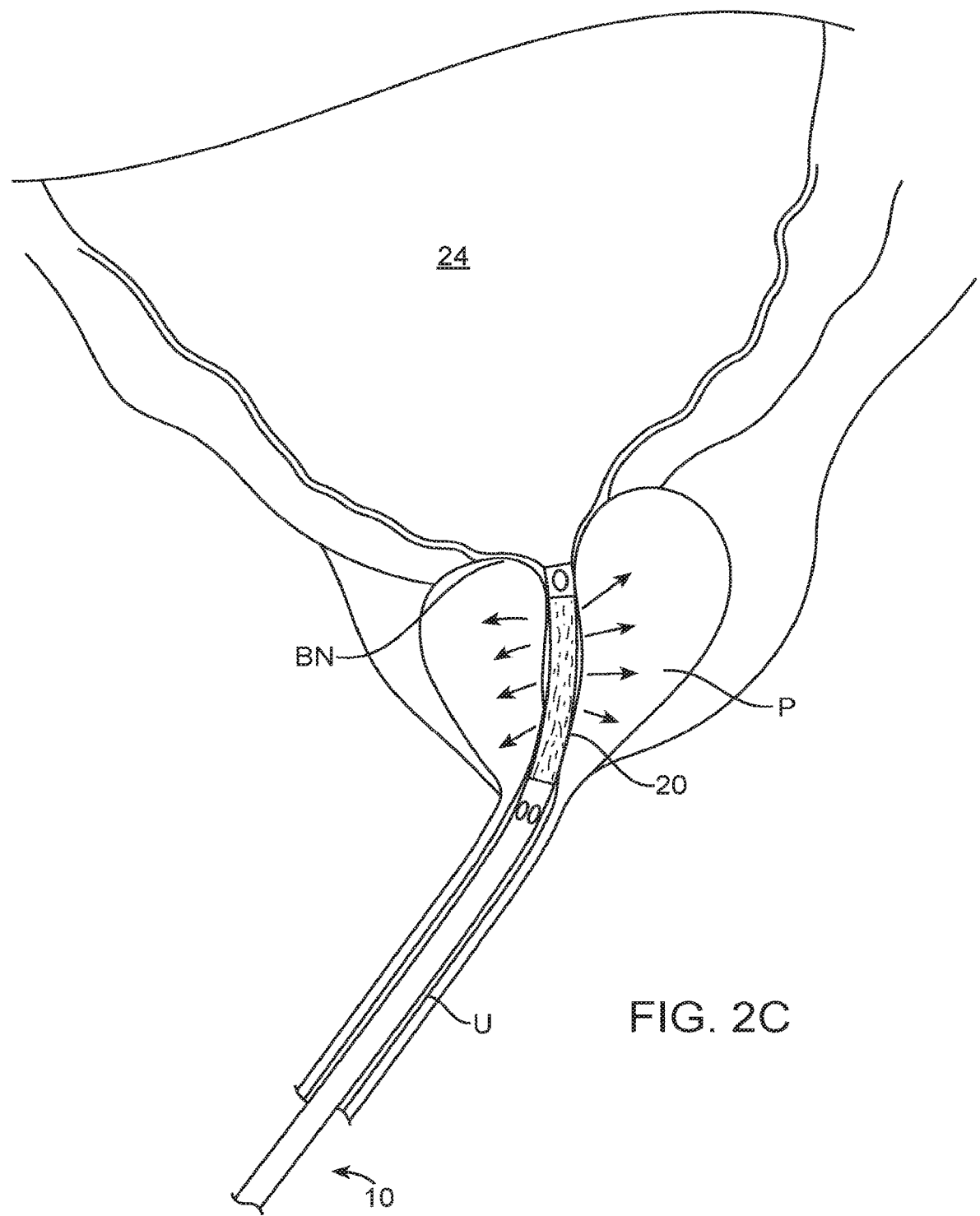
Figure 2D:
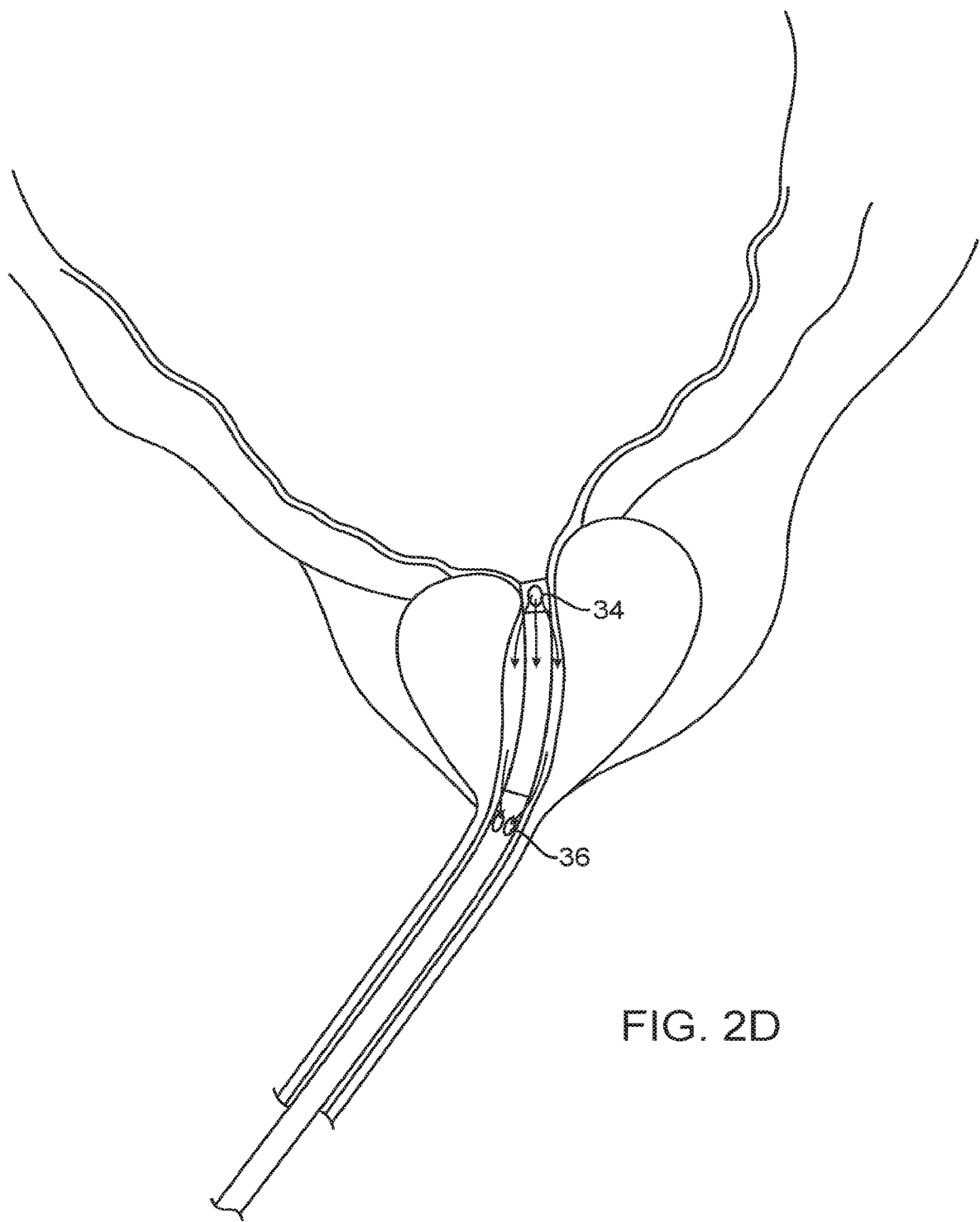

The subject matter of FIGS. 1 to 2D and the corresponding text have been incorporated by reference as described in: U.S. application Ser. No. 12/700,568, filed Feb. 4, 2010, now U.S. Pat. No. 9,232,959, issued Jan. 12, 2016; and International Application No. PCT/US2011/023781, filed on Apr. 8, 2007, published as WO2011097505 on Nov. 8, 2011; the full disclosures of which have been previously incorporated herein by reference.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft will include an energy source positioned in the energy delivery region 20, where the energy source can be any one of a number of specific components as discussed in more detail below. Distal to the energy delivery region, an inflatable anchoring balloon 24 will be positioned at or very close to the distal end 14 of the shaft. The balloon will be connected through one of the axial lumens to a balloon inflation source 26 connected through the hub 18. In addition to the energy source 22 and the balloon inflation source 26, the hub will optionally further include connections for an infusion/flushing source 28, an aspiration (a vacuum) source 30, and/or an insufflation (pressurized C02 or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, although certain positions may result in particular advantages described herein, and that the lumens and delivery means could be provided by additional catheters, tubes, and the like, for example including coaxial sleeves, sheathes, and the like which could be positioned over the shaft 12.

While the present embodiments are described with reference to the human prostate, it is understood that they may be used to treat mammal prostates in general. Referring now to FIGS. 2A-2D, the prostatic tissue debulking device 10 is introduced through the male urethra U to a region within the prostate P which is located immediately distal to the bladder B. The anatomy is shown in FIG. 2A. Once the catheter 10 has been positioned so that the anchoring balloon 24 is located just distal of the bladder neck BN (FIG. 2B) the balloon can be inflated, preferably to occupy substantially the entire interior of the bladder, as shown in FIG. 2C. Once the anchoring balloon 24 is inflated, the position of the prostatic tissue debulking device 10 will be fixed and stabilized within the urethra U so that the energy delivery region 20 is positioned within the prostate P. It will be appreciated that proper positioning of the energy delivery region 20 depends only on the inflation of the anchoring balloon 24 within the bladder. As the prostate is located immediately proximal to the bladder neck BN, by spacing the distal end of the energy delivery region very close to the proximal end of the balloon, typically within the range from 0 mm to 5 mm, preferably from 1 mm to 3 mm, the delivery region can be properly located. After the anchoring balloon 24 has been inflated, energy can be delivered into the prostate for debulking, as shown by the arrows in FIG. 2. Once the energy has been delivered for a time and over a desired surface region, the energy region can be stopped and the prostate will be debulked to relieve pressure on the urethra, as shown in FIG. 2D. At that time, a flushing fluid may be delivered through port 34 and aspirated into port 36, as shown in FIG. 2D. Optionally, after the treatment, the area could be cauterized using a cauterizing balloon and/or stent which could be placed using a modified or separate catheter device.

Figure 3A:
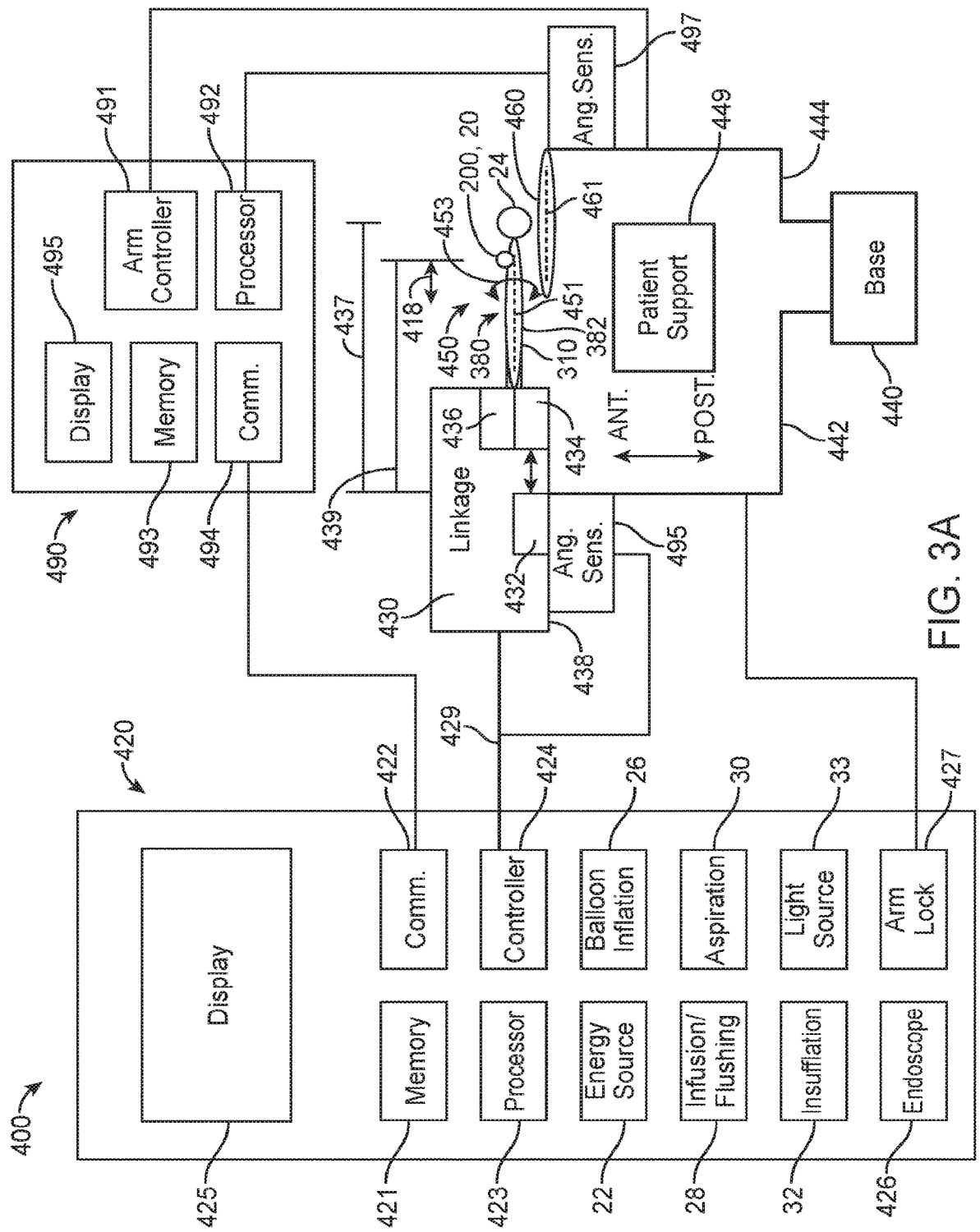
FIGS. 3A and 3B show a system to treat a patient in accordance with embodiments.
Figure 3B:
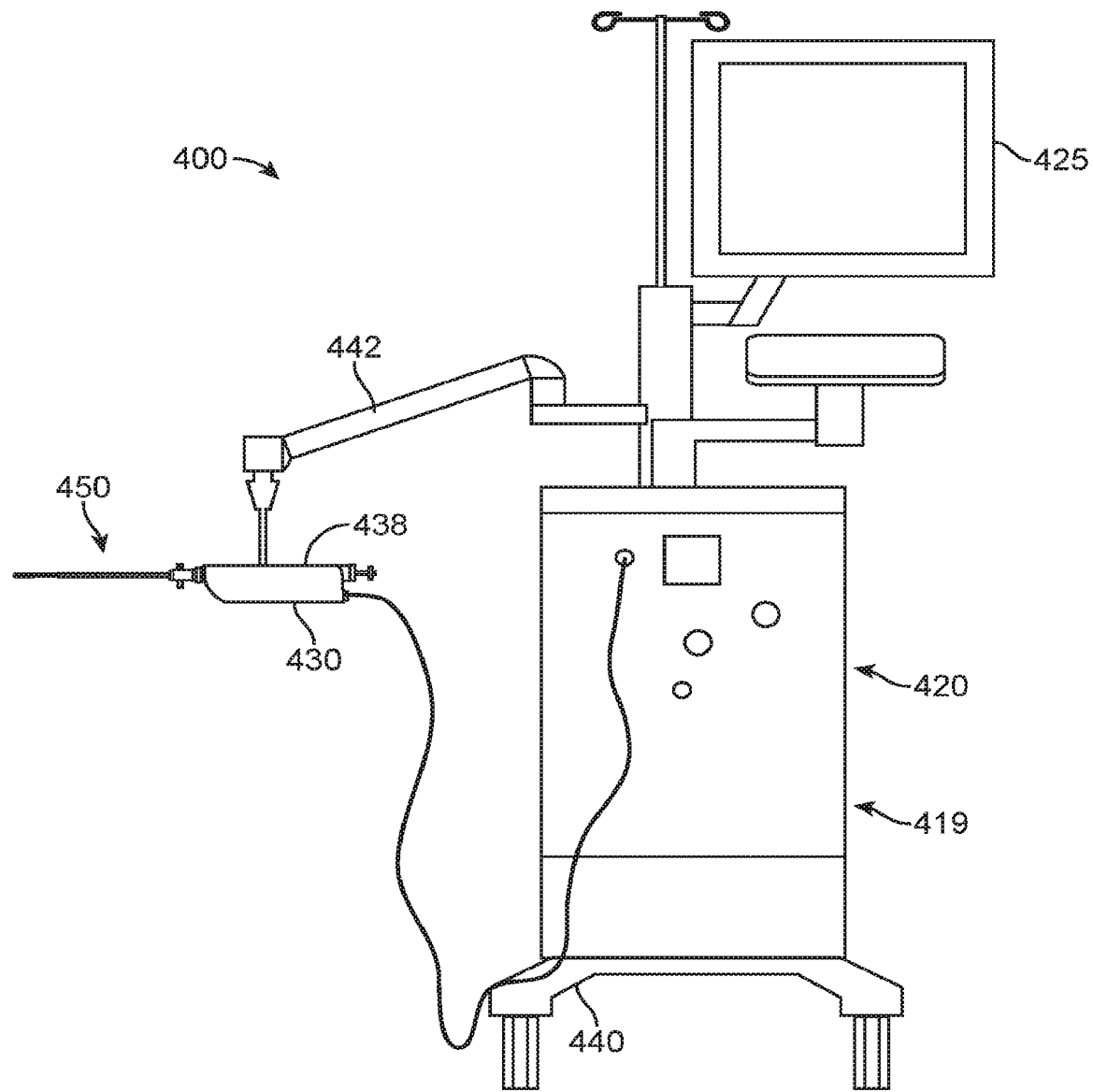

FIGS. 3A and 3B show a system to treat a patient in accordance with embodiments. The system 400 comprises a treatment probe 450 and may optionally comprise an imaging probe 460. The treatment probe 450 is coupled to a console 420 and a linkage 430. The imaging probe 460 is coupled to an imaging console 490. The patient treatment probe 450 and the imaging probe 460 can be coupled to a common base 440. The patient is supported with the patient support 449. The treatment probe 450 is coupled to the base 440 with an arm 442. The imaging probe 460 is coupled to the base 440 with an arm 444.

The patient is placed on the patient support 449, such that the treatment probe 450 and ultrasound probe 460 can be inserted into the patient. The patient can be placed in one or more of many positions such as prone, supine, upright, or inclined, for example. In many embodiments, the patient is placed in a lithotomy position, and stirrups may be used, for example. In many embodiments, the treatment probe 450 is inserted into the patient in a first direction on a first side of the patient, and the imaging probe is inserted into to the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each arm may comprise a substantially unlocked configuration such the probe can be desirably rotated and translated in order to insert the probe into to the patient. When a probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In many embodiments, the treatment probe 450 is coupled to the imaging probe 460. In order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In many embodiments, the arm 442 is a movable and lockable arm such that the treatment probe 450 can be positioned in a desired location in a patient. When the probe 450 has been positioned in the desired location of the patient, the arm 442 can be locked with an arm lock 427. The imaging probe can be coupled to base 440 with arm 444, can be used to adjust the alignment of the probe when the treatment probe is locked in position. The arm 444 may comprise a lockable and movable probe under control of the imaging system or of the console and of the user interface, for example. The movable arm 444 may be micro-actuable so that the imaging probe 440 can be adjusted with small movements, for example a millimeter or so in relation to the treatment probe 450.

In many embodiments the treatment probe 450 and the imaging probe 460 are coupled to angle sensors so that the treatment can be controlled based on the alignment of the imaging probe 460 and the treatment probe 450. An angle sensor 495 is coupled to the treatment probe 450 with a support 438. An angle sensor 497 is coupled to the imaging probe 460. The angle sensors may comprise one or more of many types of angle sensors. For example, the angle sensors may comprise goniometers, accelerometers and combinations thereof. In many embodiments, angle sensor 495 comprises a 3-dimensional accelerometer to determine an orientation of the treatment probe 450 in three dimensions. In many embodiments, the angle sensor 497 comprises a 3-dimensional accelerometer to determine an orientation of the imaging probe 460 in three dimensions. Alternatively or in combination, the angle sensor 495 may comprise a goniometer to determine an angle of treatment probe 450 along an elongate axis of the treatment probe. Angle sensor 497 may comprise a goniometer to determine an angle of the imaging probe 460 along an elongate axis of the imaging probe 460. The angle sensor 495 is coupled to a controller 424. The angle sensor 497 of the imaging probe is coupled to a processor 492 of the imaging system 490. Alternatively, the angle sensor 497 can be coupled to the controller 424 and also in combination.

The console 420 comprises a display 425 coupled to a processor system in components that are used to control treatment probe 450. The console 420 comprises a processor 423 having a memory 421. Communication circuitry 422 is coupled to processor 423 and controller 424. Communication circuitry 422 is coupled to the imaging system 490. The console 420 comprises components of an endoscope 426 is coupled to anchor 24. Infusion flashing control 28 is coupled to probe 450 to control infusion and flushing. Aspiration control 30 is coupled to probe 450 to control aspiration. Endoscope 426 can be components of console 420 and an endoscope insertable with probe 450 to treat the patient. Arm lock 427 of console 420 is coupled to arm 422 to lock the arm 422 or to allow the arm 422 to be freely movable to insert probe 450 into the patient.

The console 420 may comprise a pump 419 coupled to the carrier and nozzle as described herein.

The processor, controller and control electronics and circuitry can include one or more of many suitable components, such as one or more processor, one or more field-programmable gate array (FPGA), and one or more memory storage devices. In many embodiments, the control electronics controls the control panel of the graphic user interface (hereinafter "GUI") to provide for pre-procedure planning according to user specified treatment parameters as well as to provide user control over the surgery procedure.

The treatment probe 450 comprises an anchor 24. The anchor 24 anchors the distal end of the probe 450 while energy is delivered to energy delivery region 20 with the probe 450. The probe 450 may comprise a nozzle 200 as described herein. The probe 450 is coupled to the arm 422 with a linkage 430.

The linkage 430 comprises components to move energy delivery region 20 to a desired target location of the patient, for example, based on images of the patient. The linkage 430 comprises a first portion 432 and a second portion 434 and a third portion 436. The first portion 432 comprises a substantially fixed anchoring portion. The substantially fixed anchoring portion 432 is fixed to support 438. Support 438 may comprise a reference frame of linkage 430. Support 438 may comprise a rigid chassis or frame or housing to rigidly and stiffly couple arm 442 to treatment probe 450. The first portion 432 remains substantially fixed, while the second portion 434 and third portion 436 move to direct energy from the probe 450 to the patient. The first portion 432 is fixed to the substantially constant distance 437 to the anchor 24. The substantially fixed distance 437 between the anchor 24 and the fixed first portion 432 of the linkage allows the treatment to be accurately placed. The first portion 432 may comprise the linear actuator to accurately position the high pressure nozzle in treatment region 20 at a desired axial position along an elongate axis of probe 450.

The elongate axis of probe 450 generally extends between a proximal portion of probe 450 near linkage 430 to a distal end having anchor 24 attached thereto. The third portion 436 controls a rotation angle around the elongate axis. During treatment of the patient, a distance 439 between the treatment region 20 and the fixed portion of the linkage varies with a reference distance 439. The distance 439 adjusts in response to computer control to set a target location along the elongate axis of the treatment probe referenced to anchor 24. The first portion of the linkage remains fixed, while the second portion 434 adjusts the position of the treatment region along the axis. The third portion of the linkage 436 adjusts the angle around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging system 490 comprises a memory 493, communication circuitry 494 and processor 492. The processor 492 in corresponding circuitry is coupled to the imaging probe 460. An arm controller 491 is coupled to arm 444 to precisely position imaging probe 460.

Figure 4A:
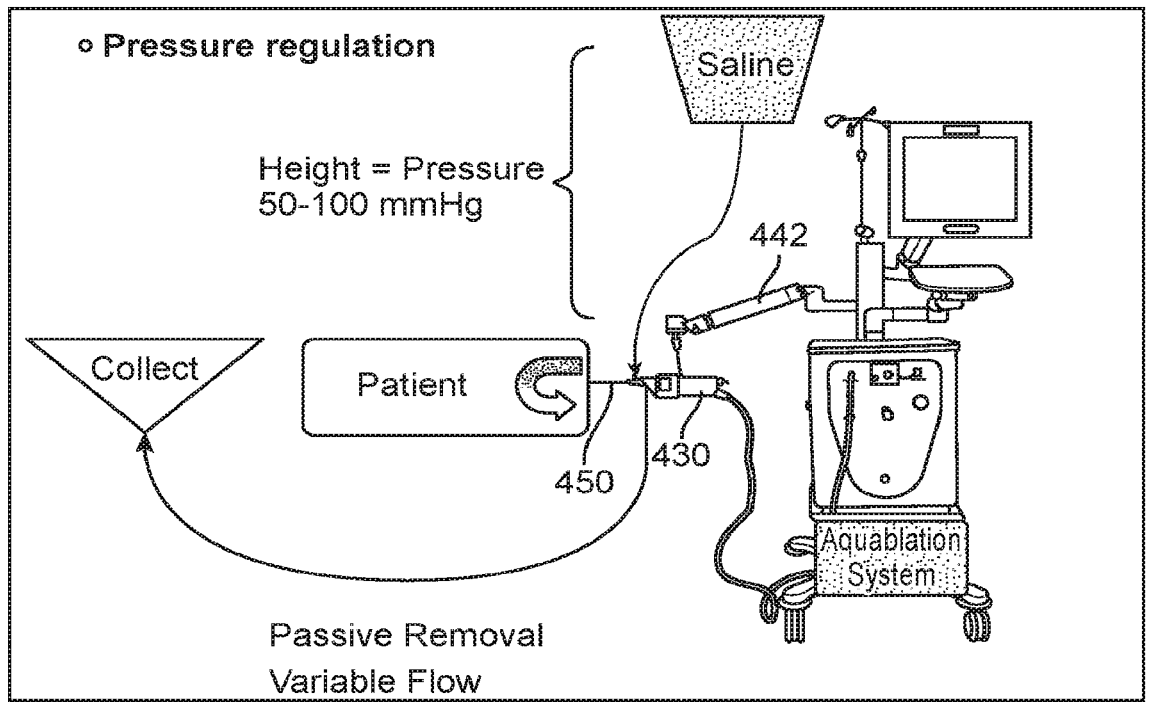
FIG. 4A shows pressure regulation of the surgical site with a substantially constant pressure and variable flow, in accordance with embodiments.

FIG. 4A shows pressure regulation of the surgical site with a substantially constant pressure and variable flow. The saline bag is placed at a height to provide substantially constant pressure regulation. The bag of saline can be placed at a height corresponding to about 50 to 100 mm of Mercury (hereinafter "mmHg"). The saline bag is coupled to the irrigation port as described herein. A collection bag is coupled to one or more of the irrigation port, the aspiration port, or the suction port as described herein. The collection bag collects tissue removed with the water jet ablation probe 450 as described herein.

Figure 4B:
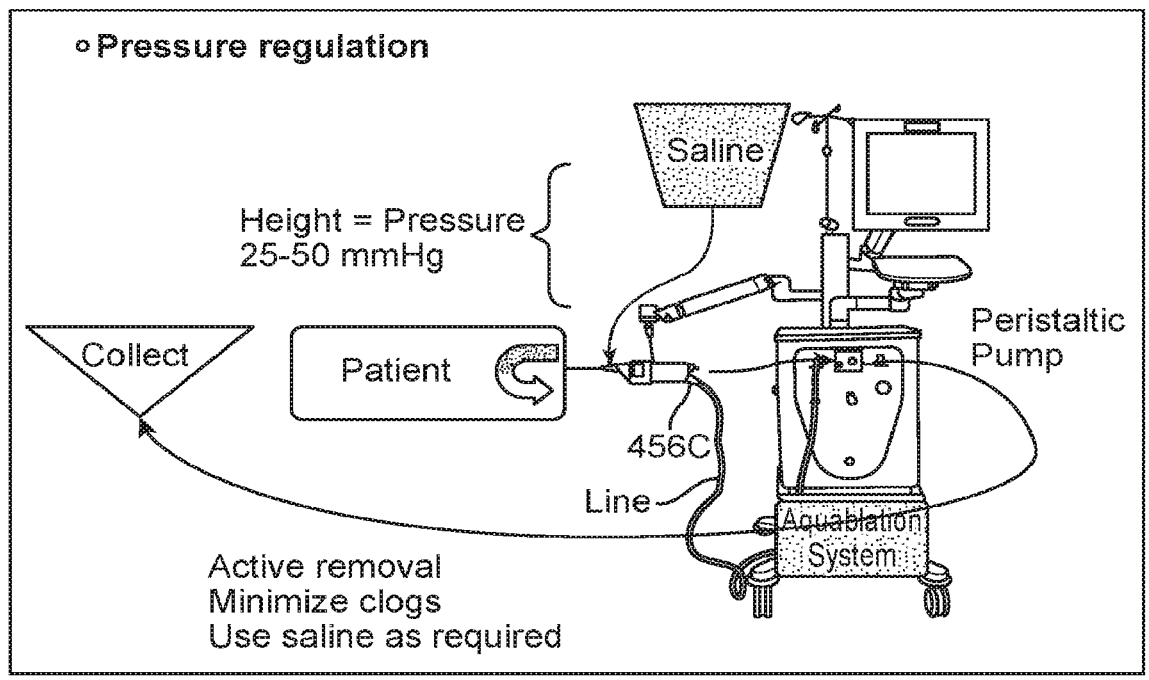
FIG. 4B shows flow regulation of the surgical site with a pump providing a substantially fixed fluidic flow and a substantially constant pressure, in accordance with embodiments.

FIG. 4B shows flow fluidic regulation of the surgical site with a pump providing a substantially fixed fluidic flow. A pump removes fluid from the surgical site at a substantially fixed flow rate. The pump may comprise a peristaltic pump, for example. The pump is configured to remove fluid at the substantially the same rate or greater than Aquablation™ saline flow rate, in order to inhibit pressure build up at the surgical site. The peristaltic pump can be coupled to the aspiration port of the manifold comprising tissue removal port 456C as described herein, for example. Providing the pump having the flow rate that is at least the flow rate of the tissue ablation jet provides improve suction as ablated tissue that might otherwise block the tissue removal openings and channel can be subjected to greater amounts of pressure when the pump maintains the substantially fixed flow rate in order to remove the material that would otherwise block the channel.

The irrigation flow from the saline bag may remain open in order to provide at least two functions: 1) maintain pressure based on the height of the saline bag; and 2) provide a safety check valve in case the peristaltic pump is not functioning correctly as visually a person would see flow entering the bag as a pink color.

In alternate embodiments, the flow of the pump comprises a variable rate in order to provide a substantially constant pressure within the patient near the surgical site. The active sensing of pressure of the treated organ and variable flow rate of the pump may comprise a closed loop pressure regulation system. The pump can be coupled to a sensor such as a pressure sensor, and the flow rate varied to maintain substantially constant pressure. The pressure sensor can be located in one or more of many places such as on the treatment probe, within the aspiration channel of the probe, in a recess of an outer surface the probe, on an inner surface of the probe coupled to the surgical site, or near the inlet to the pump on the console for example.

Figure 5A:
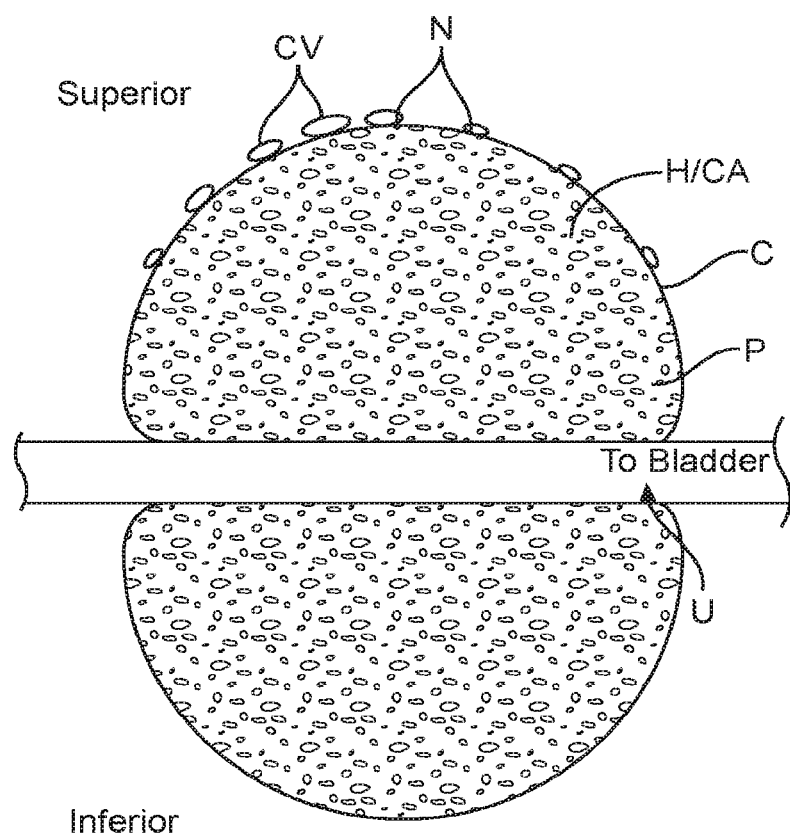
FIG. 5A shows an organ suitable for incorporation in accordance with many embodiments.

FIG. 5A shows an organ suitable for incorporation in accordance with embodiments. The organ may comprise one or more of many organs as described herein, for example, the prostate P. In many embodiments the organ comprises a capsule C and tissue contained within the capsule and capsular vessels CV and nerves N located on an exterior of the capsule, for example. In many embodiments the organ comprises a prostate. The prostate may comprise hyperplasia H such as benign prostate hyperplasia or cancer CA and combinations thereof, for example. In many embodiments the hyperplasic tissue may comprise tissue located within the patient in which the cancer may not have been detected. In many embodiments capsular vessels and nerves extend along an exterior surface of the prostate. In many embodiments the hyperplasic tissue can be located superiorly on the prostate. In the many embodiments the hyperplasic tissue may comprise tissue of unknown specificity with respect to whether the tissue comprises cancerous tissue or benign tissue.

Figure 5B:
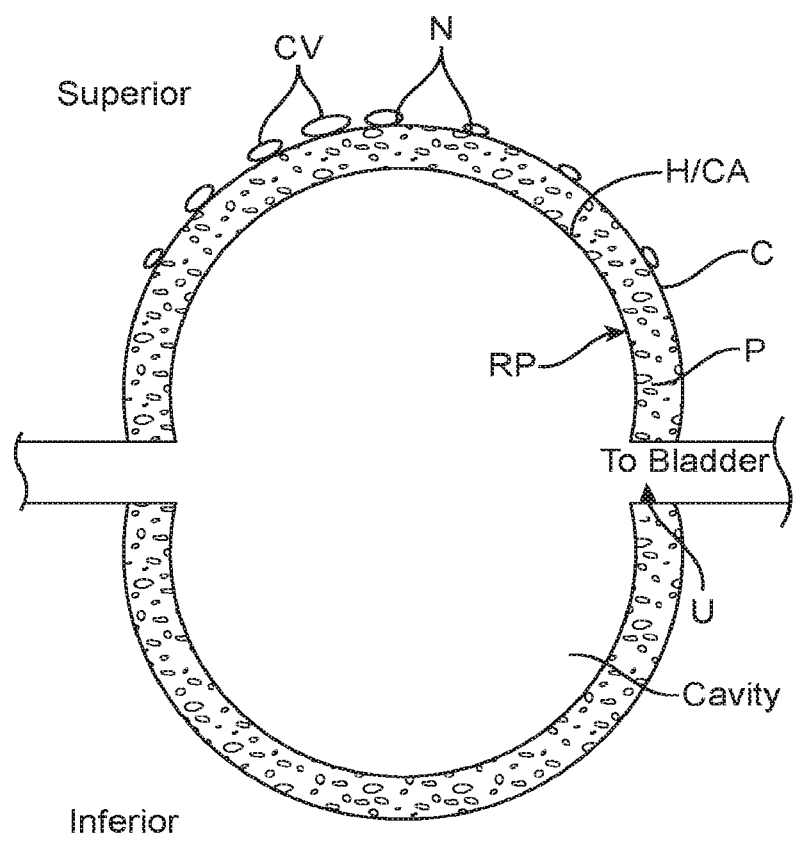
FIG. 5B shows the prostate of FIG. 5A treated with an apparatus in accordance with many embodiments.

FIG. 5B shows the prostate P of FIG. 5A treated with an apparatus in accordance with embodiments. In many embodiments the tissue of the prostate is removed in accordance with a tissue removal profile RP. The tissue removal profile may comprise of predetermined tissue removal profile based on image-guided tissue removal as described herein, for example. Alternatively the tissue removal profile may comprise of removal profile of tissue removed with a handheld tissue removal apparatus. In many embodiments the tissue of the organ, such as the prostate, is removed to within the capsule C in order to decrease the distance from the tissue removable profile to the exterior of the capsule, for example.

In many embodiments a tissue treatment apparatus, such as a catheter having an expandable support, is placed within the organ in order to engage the remaining tissue that defines the removal profile and the capsule with an expandable support.

In many embodiments the tissue within the organ is removed such that the capsule of the organ, such as the prostate, remains intact which has the advantage of retaining the integrity of the capsule or vessel's nerves which may extend around an exterior surface of the capsule. In many embodiments this removal of the capsular tissue is inhibited in order to retain the integrity of the capsule and the corresponding tissue structures such as capsular vessels and/or nerves. The tissue removal profile may define a cavity corresponding to the removed tissue of the organ such as the prostate. In many embodiments a portion of the tissue near the capsule may comprise tissue, such as cancerous tissue or tissue identified as having a probability of being cancerous tissue, such as hyperplasic tissue in the superior portion or other portion of the organ. The remaining tissue can be treated in one or more of many ways as described herein. In many embodiments the remaining tissue, which may comprise remaining hyperplasic tissue, is treated with radiation.

Figure 5C:
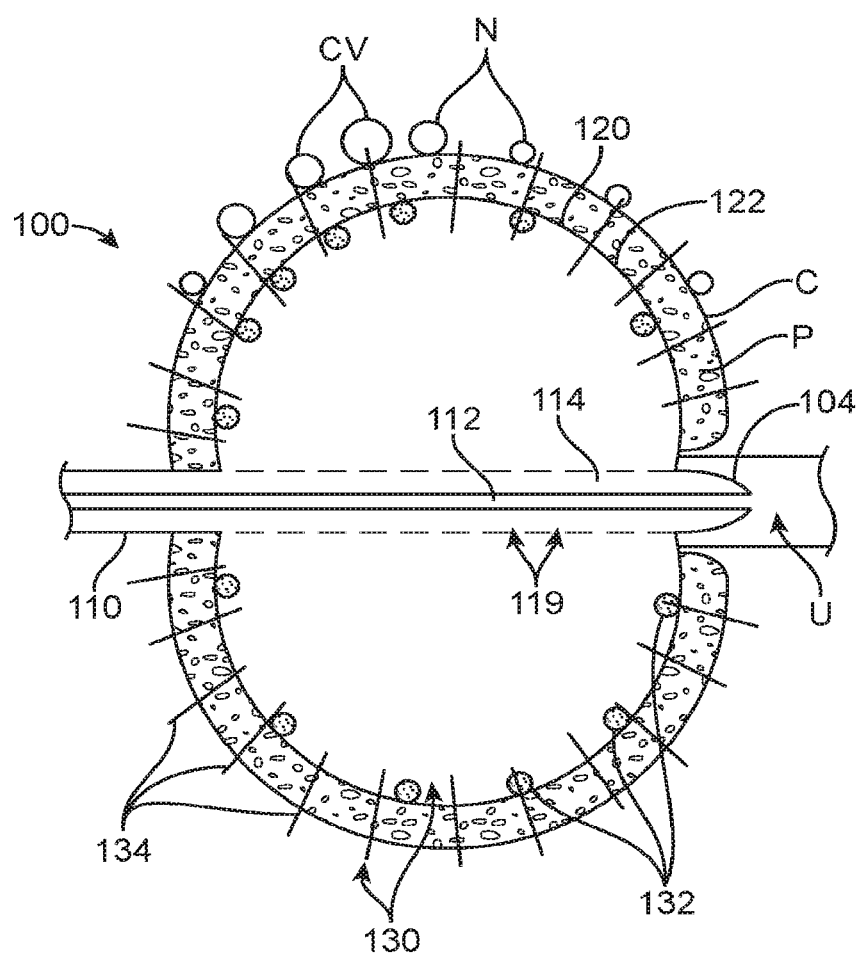
FIG. 5C shows tissue of the organ treated with radiation with an expandable support and radiation therapy in accordance with many embodiments.

FIG. 5C shows tissue of the organ treated with radiation with an expandable support and radiation therapy in accordance with embodiments. An expandable support 120 may comprise one or more of many structures to allow the support to expand from a first narrow profile configuration to a second expanded profile configuration. The expandable support 120 can be located on a distal end of an elongate tubular member 110 such as a catheter, for example. In many embodiments the expandable support 120 is inserted into a channel to access the organ, for example urethra U, as described herein. The expandable support can be inserted through an external opening of the urethra into the patient and, subsequently, in the narrow profile configuration and subsequently expanded to a wide profile configuration, as shown in FIG. 5C, in order to treat the patient. The expandable support may comprise of balloon 122, for example. The elongate tubular member 110 may comprise a plurality of channels in fluidic communication with the expandable support in a distal end of the elongate tubular member. An internal end 104 of the elongate tubular member of the treatment apparatus 100 can be inserted into an external opening of the urethra and advance towards the bladder, for example, past the prostate such that the expandable support 120 is positioned in the cavity provided with a treatment and removal of the organ such as the prostate. The expandable support 120 can be inflated from a narrow profile configuration to an expanded profile configuration in order to treat the remaining tissue. The remaining tissue can be treated in one or more of many ways with the expandable support. For example, the remaining tissue may be cauterized, treated with radiation and combinations thereof. In many embodiments the remaining tissue is treated with radiation. The radiation can be provided in one or more of many ways with a radioactive material. For example, the radioactive material may comprise seeds 132 of radioactive material 130 located on the expandable support such that the seeds of radioactive material are urged radially outward, away from the expandable support from the narrow configuration to the expanded profile configuration in order to engage the remaining tissue of the organ. The radioactive seeds and material can be left in engagement with the tissue of the organ for a plurality of days, for example three to five days, depending upon the intended dosage of radiation with the treatment. Upon completion of the treatment the lumen can be with—the expandable support can be retracted and the expandable support withdrawn from the patient and a narrow profile configuration from the prostate and the urethra, for example.

The radiation can be provided in one or more of many ways. For example, the radiation may comprise seeds; the radiation may comprise spikes; the radiation may comprise fluid injected into a lumen of a balloon, for example, and combinations thereof. The radioactive barbs 134, or spikes, can have the advantage of extending through the remaining tissue and through the exterior of the capsule in order to treat residual tissue which may comprise cancerous tissue at an early stage of metastases in order to inhibit spread of the metastatic cancerous tissue. For example, cancerous tissue located on an exterior of the capsule. Alternatively, or in combination, the barbs may comprise a releasable structure such that the barbs can remain within the tissue when the expandable support has been retracted away from the tissue. In many embodiments the radiation therapy can be provided by inflating a balloon with a radioactive fluid for a plurality of days such that the radioactive fluid remains within a balloon inflated within the organ, such as the prostate, for the plurality of days. Upon completion of an intended dosage of radiation the radioactive fluid can be removed from the balloon and the balloon and elongate tubular member 110 withdrawn from the patient. In many embodiments the radiation therapy can be provided with seeds coupled to the expandable support such that the seeds are in engagement with the remaining tissue for a plurality of days. Upon completion of the treatment the expandable support can be retracted and the seeds retracted with the expandable support such that the radiation therapy is not implanted in the patient and the patient has the therapy end upon removal of the radiation with the expandable support.

The elongate tubular member 110 may comprise a first lumen 112 and a second lumen 114, for example, in which the first lumen allows the flow of urine from the urethra to pass from an internal end 104 of the apparatus 100 to an external end 102 in which the internal end is positioned toward the bladder from the prostate and the external end 102 is positioned external to an external opening of the urethra. When the expandable support 120 comprises the expanded configuration, urine is allowed to pass from the first lumen 112 to the external opening in order to allow the passage of urine. The second lumen 114 can be used to inflate the expandable support, for example, in which a plurality of openings 119 is provided to allow the second lumen 114 to be used to inflate the expandable support. The external end 102 of the elongate tubular member can be provided with structures to allow injection and retention of the fluid filling the expandable support, such as a balloon. The expandable support can be configured to urge outwardly, away from the elongate tubular member, in order to engage the remaining tissue with at least some force in order to anchor the expandable support and the elongate tubular member in the prostate. Alternatively or in combination, anchor structures can be provided which anchor the treatment apparatus 100 to the bladder of the patient in order to inhibit stress upon the treated tissue with the expandable support 100.

The expandable support 120 can have the advantage of inhibiting bleeding and blood loss and promoting healing even when provided without radiation therapy, for example.

Figure 6A:
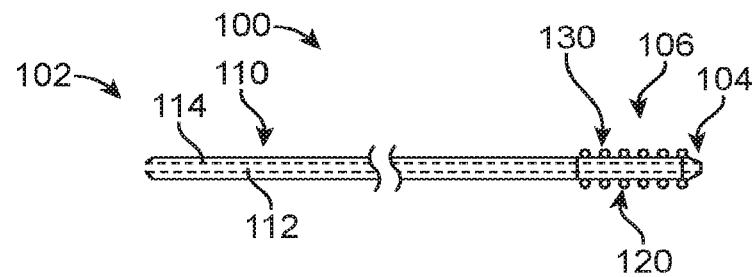
FIG. 6A shows a treatment apparatus in accordance with many embodiments.

FIG. 6A shows a treatment apparatus 100 in accordance with embodiments. The treatment apparatus 100 comprises an internal end 104 and an external end 102. The internal end 104 is configured for advancement within a channel which may comprise a surgically formed channel or a naturally occurring body channel and combinations thereof. The apparatus 100 comprises an elongate tubular member 110 and an expandable support 120. The apparatus 100 may comprise of radioactive substance 130 located on an expandable support 120.

The elongate tubular member 110 may comprise a catheter, for example, and the catheter 110 may comprise a plurality of lumens, for example, a first lumen 112 and a second lumen 114. The first lumen 112 may extend from the external end 102 to the internal end 104, for example, in order to allow the passage of a bodily fluid, such as urine. The second channel 114 can extend from the external end 102 to the expandable support 130 in order to expand the expandable support 130 from a first narrow profile configuration to a second expanded profile, or wide profile, configuration. The narrow profile configuration allows the expandable support to be advanced within an internal channel or lumen of the patient, for example.

The apparatus 100 may comprise electrodes for electrocautery in the expanded profile configuration, for example.

The apparatus 100 can be injected with saline to structure 120. For example, balloon 122 can be injected with a non-radioactive substance such as saline.

Figure 6B:
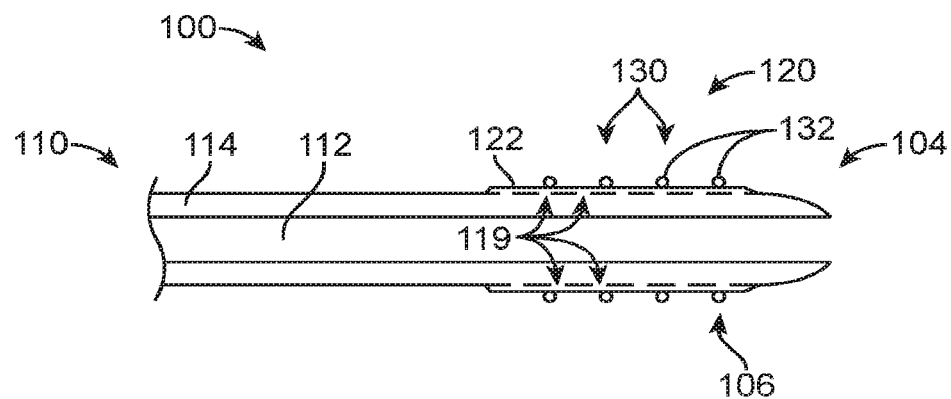
FIG. 6B shows internal end in a narrow profile configuration in accordance with many embodiments.

FIG. 6B shows internal end 104 in a narrow profile configuration 106. The expandable support 120 comprises a radioactive substance 130. The expandable support 120 may comprise an expandable balloon 122. The radioactive substance 130 may comprise a plurality of radioactive seeds 132. A plurality of openings 119 provides fluidic communication of the second lumen 114 with the expandable balloon 122. When a fluid is injected into the external end 102 of the elongate tubular member 110 the balloon 122 is urged radially outward with fluid passing through openings 119.

Figure 6C:
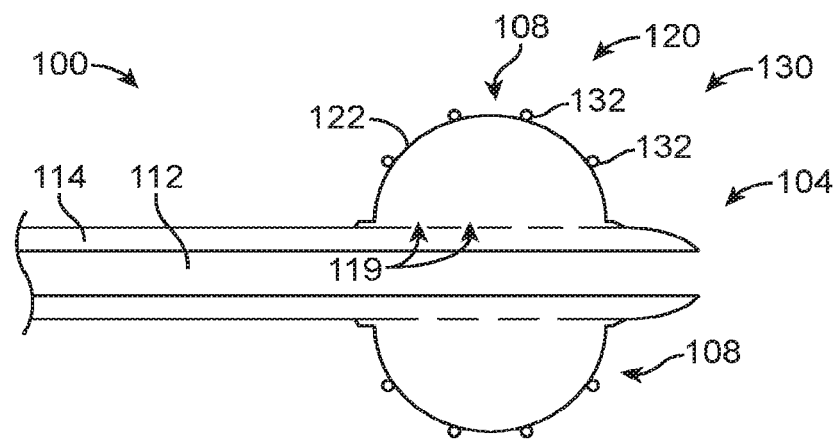
FIG. 6C shows the internal end in an expanded wide profile configuration in accordance with many embodiments.

FIG. 6C shows the internal end 104 in an expanded wide profile configuration 108. The expanded wide profile configuration 108 is configured to engage tissue with the expanded wide profile configuration and with fluid injected into second lumen 114. In the expanded wide profile configuration the radioactive substance 130 is positioned in proximity to the remaining tissue of the organ. The radioactive substance 130 may comprise radioactive seeds 132 distributed at a plurality of locations on the expandable support 130.

In many embodiments the plurality of radioactive seeds are situated at a plurality of locations on the expandable support 120 in order to provide a therapeutic treatment profile of radiation to the tissue. The plurality of seeds 132 can be positioned at predetermined locations on the support 120.

In the narrow profile configuration 106 the plurality of seeds are positioned closer to each other than in the wide profile configuration 108. In the wide profile configuration the plurality of seeds are spaced apart in order to provide a therapeutic treatment profile to the tissue near the capsule.

Figure 7A:
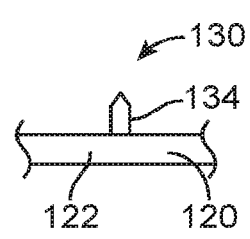
FIG. 7A shows a radioactive substance comprising a barb configured to penetrate tissue in accordance with many embodiments.

FIG. 7A shows a radioactive substance 130 comprising a barb 134 configured to penetrate tissue. The barb 134 comprises a first end on an outer surface of the expandable support 120. The barb 134 may comprise a base coupled to and in contact with the support 120 and a distal end comprising a pointed tip shaped to penetrate tissue. The barb 134 can comprise an elongate distance extending from the base to the tip and the elongate distance can be sized to penetrate the remaining tissue and the capsule in order to position the tip outside the capsule in order to treat tissue located outside of the capsule or surface, adjacent to capsule or vessels and nerves. Alternatively, the tip and length of the barb can be sized to inhibit penetration of the capsule. In many embodiments the barb 134 is configured for implantation in the tissue. The barb 134 can be releasably attached to the expandable support 120 such that when the support 120 expands and barb 134 is placed in tissue the support 120 can be retracted and leave the barb 134 in the tissue as an implant. The barb 134 can be placed on an outer surface of the support 120 and can be loosely coupled on the outer surface of the support 120 for implantation in the tissue.

Alternatively, the barb 134 can be affixed to the support 120, for example, with a suitable glue or mechanical fixation.

Figure 7B:
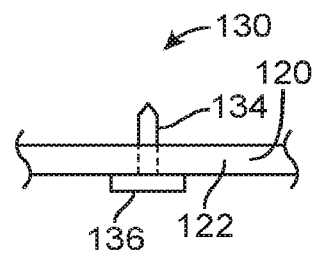
FIG. 7B shows barb configured for retraction from the tissue in accordance with many embodiments.

FIG. 7B shows barb 134 configured for retraction from the tissue. The radioactive substance 130 comprising the barb 134 can be withdrawn from the tissue when the support 120 is retracted. While the barb 134 can be configured for retraction in many ways and many embodiments, the support 120 is penetrated with barb 134. 136 is affixed to the barb with the head 136 located on an interior surface of the support 120 in order to affix the barb 134 to the support 120. The head 136 may comprise a wide structure in order to retain the barb 134 with the expandable support 120, for example.

Figure 7C:
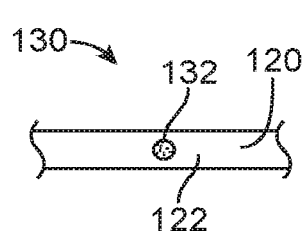
FIG. 7C shows a radioactive seed embedded in the expandable support in accordance with embodiments.

FIG. 7C shows a radioactive seed 132 embedded in the expandable support 120. The radioactive seed can be molded within the support, for example, or glued within the support.

Figure 7D:
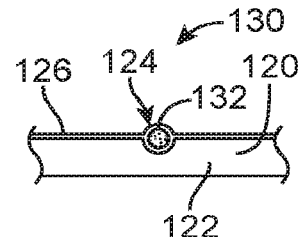
FIG. 7D shows a radioactive seed retained in a pocket of the support in accordance with embodiments.

FIG. 7D shows a radioactive seed 132 retained in a pocket 124 of the support. The pocket 124 may comprise one or more of many structures configured to retain the radioactive seed 132. For example, the pocket 124 may comprise an indentation, a slit or other structure capable of receiving the pocket, receiving the seed 132. In many embodiments a sheath 126 covers the radioactive substance 130 and the sheath can be retracted, for example. Alternatively the sheath can remain affixed over the support 120, for example.

In many embodiments the sheath 126 can be retracted to expose a barb 134 in order to implant the barb within the tissue or to allow the barb to be advanced without contacting an internal service of a lumen such as a wall of the urethra.

Figure 8A:
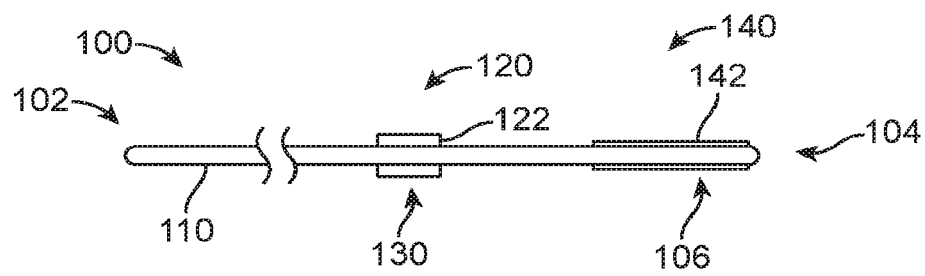
FIG. 8A is a treatment apparatus comprising an anchor in accordance with many embodiments.

FIG. 8A shows a treatment apparatus comprising an anchor 140 in accordance with embodiments. The anchor 140 may comprise of an anchoring balloon 142. The anchoring balloon 142 can be expanded with the balloon 122 in accordance with embodiments described herein. The anchor 140 and expandable support 120 comprise a narrow configuration 106 for insertion along a channel of a patient, such as a surgically formed channel or a lumen of a natural channel, such as a urethra, as described herein. In the narrow profile configuration the anchor 140 can be advanced to the bladder neck of the patient and anchored to the bladder neck in order to inhibit movement of the expandable support 120 when placed. The anchor 140 can inhibit movement of expandable support 120 in order to promote healing and decrease potential trauma to the tissue engaged with expandable support 120. For example, the external end 102 can be inadvertently drawn from the patient in use and anchor structure 120 can be tugged on and anchor 140 inhibits movement of expandable support 120.

In many embodiments, the expandable support 120 comprises the radioactive substance 130 as described herein.

Figure 8B:
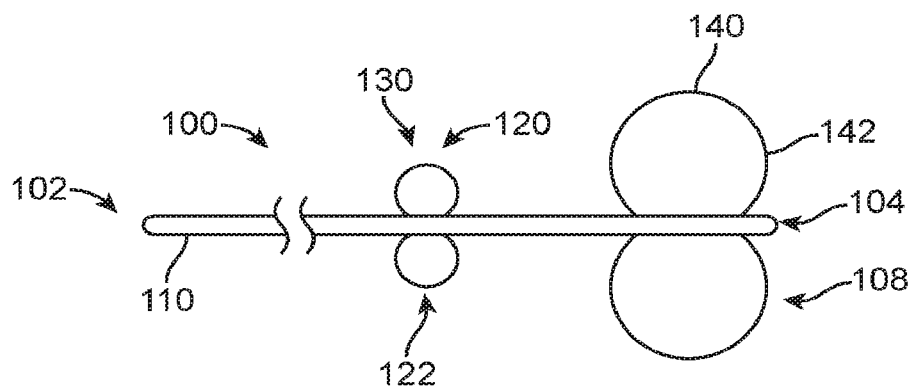
FIG. 8B shows expandable support and anchor structure in an expanded configuration in accordance with many embodiments.

FIG. 8B shows expandable support 120 and anchor structure 140 in an expanded configuration 108. In the expanded wide profile configuration 108, movement of the elongate tubular member 110 and expandable support 120 is inhibited. In the expanded profile configuration the apparatus 100 can be left in the patient for a plurality of days. For example, at least two days, three days, four days or five days in order to allow for the patent to heal and to provide treatment. The elongate tubular member 110 comprises structures as described herein, such as the first channel and the second channel.

Figure 12:
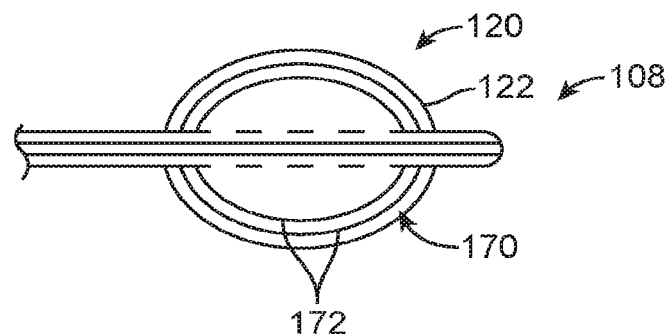
FIG. 12 shows cautery electrodes on an expandable support in accordance with many embodiments.

FIG. 12 shows cautery electrodes 170 on an expandable support 120 as described herein. The cautery electrodes may comprise bipolar electrodes 172, for example. Traces can be provided to couple the electrodes 172 to an external source of power to provide electro cautery, for example. The support 120 can be provided with a radioactive material as described herein, for example.

Figure 13:
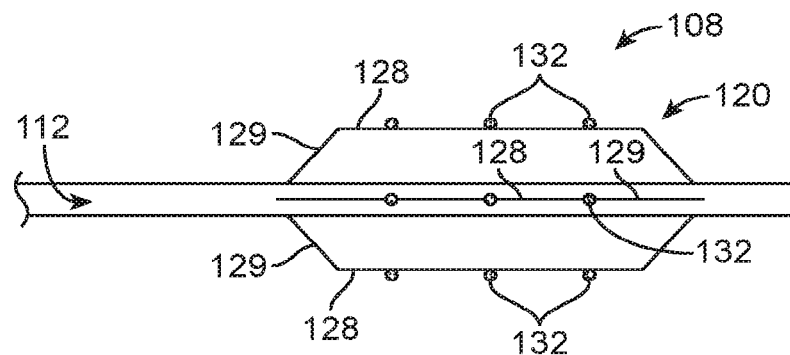
FIG. 13 shows an expandable support comprising a plurality of longitudinal struts and a plurality of transverse members in accordance with many embodiments.

FIG. 13 shows an expandable support 120 comprising a plurality of longitudinal struts 128 and a plurality of transverse members 129. The expandable support 120 may comprise radioactive substance 130 as described herein. The plurality of longitudinal struts extends longitudinally along the support. The plurality of longitudinal struts can be coupled to the transverse elements to expand and retract support 120 as described herein, for example.

The embodiments as disclosed herein can be used to collect fat cells and prostate tissue, and many other tissue types of tissue, such as tissue from other organs, for example. The embodiments as disclosed herein are well suited to detect cancer, and can be used to detect biomarkers (natural and/or synthetic), that may react and/or interact with tumor proteins, related to triggering and/or amplification of many other processes, functions, or signals indicative of malignancy and/or a degree of malignancy.

The methods and apparatus as disclosed herein are well suited for use with many other tissues in addition to the prostate. In many embodiments, a delayed or immediate reaction can be used for an instant detection and diagnosis. With embodiments related to prostate tissue for example, the sample collection and detection methods as disclosed herein allow the surgeon to treat the prostate for cancer and tailor cancer treatment based on the diagnosis after tissue collection derived from the patient's BPH treatment as the patient is still at the operating table/chair, for example.

In many embodiments, the collected tissue can be used to identify pathological condition and histological evaluation.

As used herein, the terms AquaBeam, flame, fluid flame, fluid cloud, entrainment region, and cavitation region are used interchangeably.

An apparatus for tissue removal may comprise a nozzle configured to deliver a fluid stream, wherein the fluid stream may comprise one or more of a liquid or a gas. A liquid fluid stream may comprise one or more of water or saline, for example. A liquid fluid stream may be configured to exit the nozzle in the form a liquid ablation jet, causing cavitations in the prostate tissue and dissociating the tissue into a plurality of fragments. The liquid fluid stream can be released into a liquid in which the nozzle is immersed in order to provide cavitation with shedding pulses as described herein. The liquid in which the nozzle is immersed may comprise one or more of water or saline, for example.

Figure 5D:
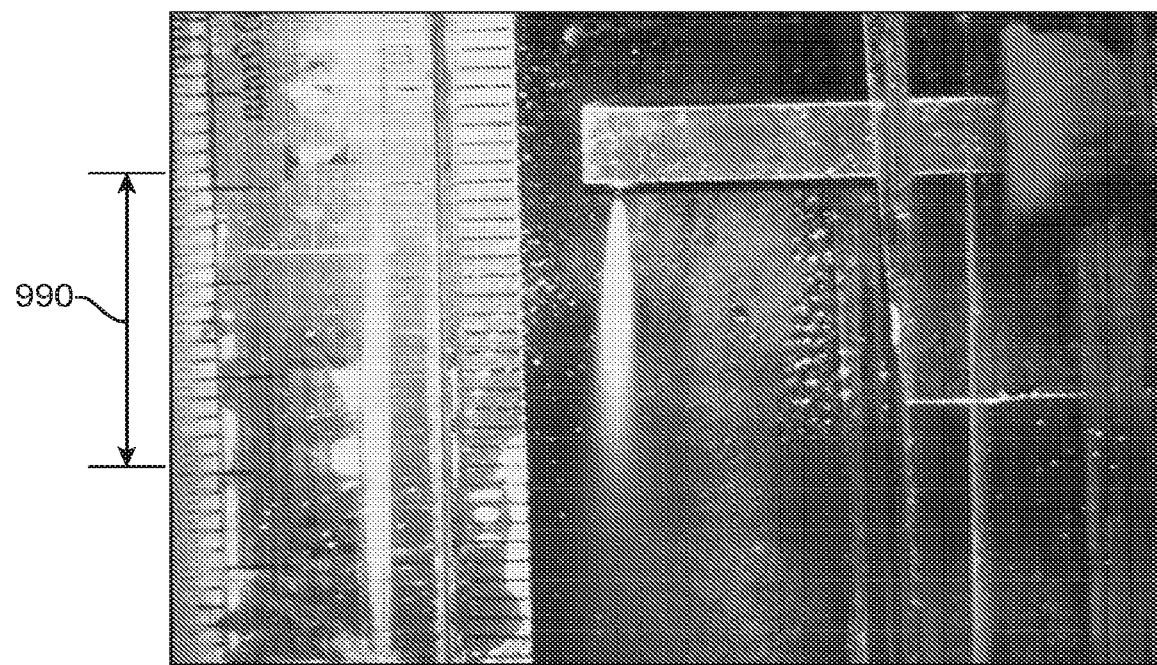
FIG. 5D shows an ablative flame visible to the human eye, in accordance with embodiments.

FIG. 5D shows an ablative flame visible to the human eye, in accordance with embodiments.

Figure 5E:
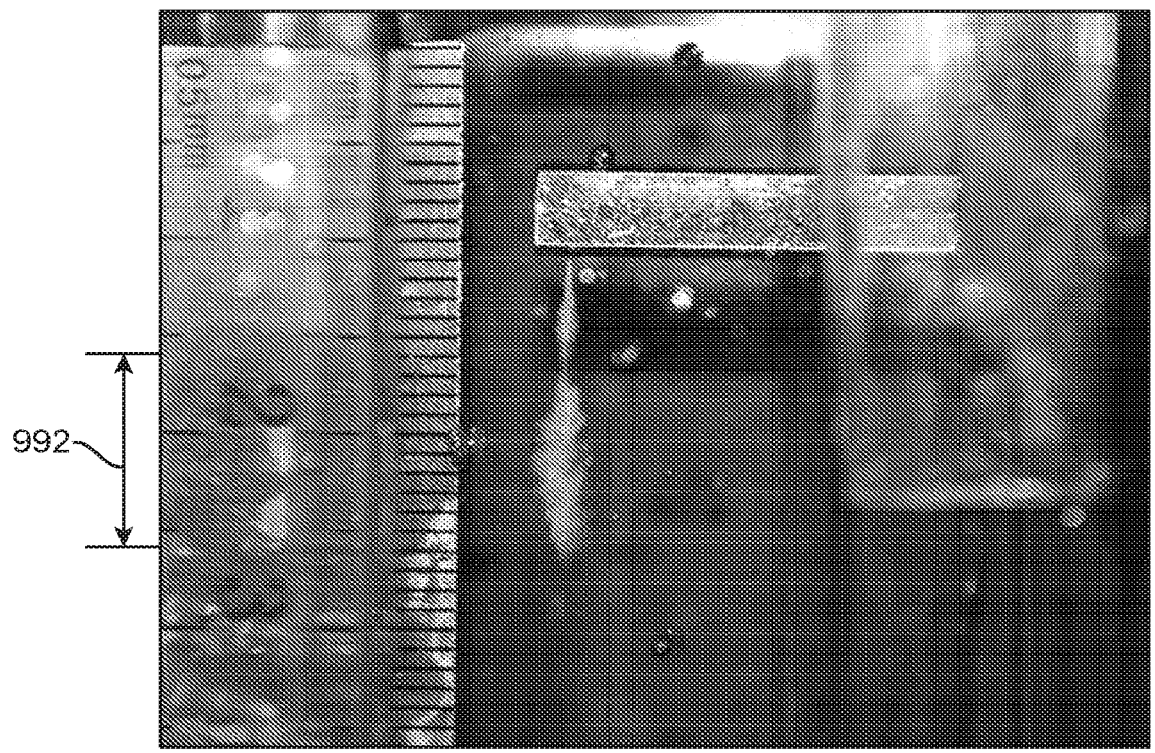
FIG. 5E shows a high speed image of the ablative flame as in FIG. 5C.

FIG. 5E shows a high speed image of the ablative flame as in FIG. 5C. The image was taken at a speed of about $\frac{1}{400}$ of a second.

The data of FIGS. 5D and 5E show that the ablative flame comprises a plurality of white clouds generated with the ablative stream when released from the nozzle. Work in relation to embodiments has shown that the cavitating cloud can shed from the jet at a characteristic shedding frequency. A length 992 of each cloud is related to the shedding frequency and the velocity of the cloud. The relatively cool ablative flame of the jet comprises a length 990 corresponding to the cutting length of the jet which can be adjusted to cut tissue to controlled depth as described herein. In many embodiments, nozzle of the jet is placed at least about a quarter of the length 992 of a shed cloud in an non-cutting configuration as shown in FIG. 5C, in order to allow the shedding cloud to substantially form prior to the cloud striking tissue. This divergence of the shed cloud to a larger cross sectional size can also provide improved tissue removal as the cloud can be distributed to a larger region of tissue and provide improved overlap among the pulses of the jet.

In addition to the impact pressure of the jet, the highly turbulent and aggressive region corresponding to the white cloud of the image contributes substantially to the ablation of tissue as described herein. The white cloud comprises a plurality of cavitation regions. When pressurized water is injected into water, small cavitations are generated in areas of low pressure in the shear layer, near the nozzle exit. The small cavitations may comprise cavitation vortices. The cavitation vortices merge with one another, forming large discrete cavitation structures that appear in the high speed images as cavitation clouds. These cavitation clouds provide effective ablation when interacting with tissue. Without being bound by any particular theory, it is believed that the cavitation clouds striking tissue cause substantial erosion of tissue related to the cavitations in combination of the high velocity fluid that defines the cavitations striking tissue.

The nozzle and pressure as described herein can be configured to provide the pulsatile clouds, for example with control of the angle of the nozzle, by a person of ordinary skill on the art based on the teachings provided herein. In many embodiments, the nozzle of the fluid delivery element comprises a cavitating jet in order to improve ablation of tissue.

The fluid delivery element nozzle and pressure can be arranged to provide a shedding frequency suitable for removal of tissue.

In many embodiments, the "white cloud" of "flame" comprises an "entrainment" region where surrounding water is drawn in or "entrained" into the jet. Work in relation to embodiments suggests that the entrainment of fluid can be related to the shedding frequency.

The shedding frequency and size of the cloud shed from the jet can be used to provide tissue ablation in accordance with embodiments. The shedding frequency can be combined with the angular sweep rate of the probe around the longitudinal axis to provide overlap of the locations where each cloud interacts with the tissue.

Figure 5F:
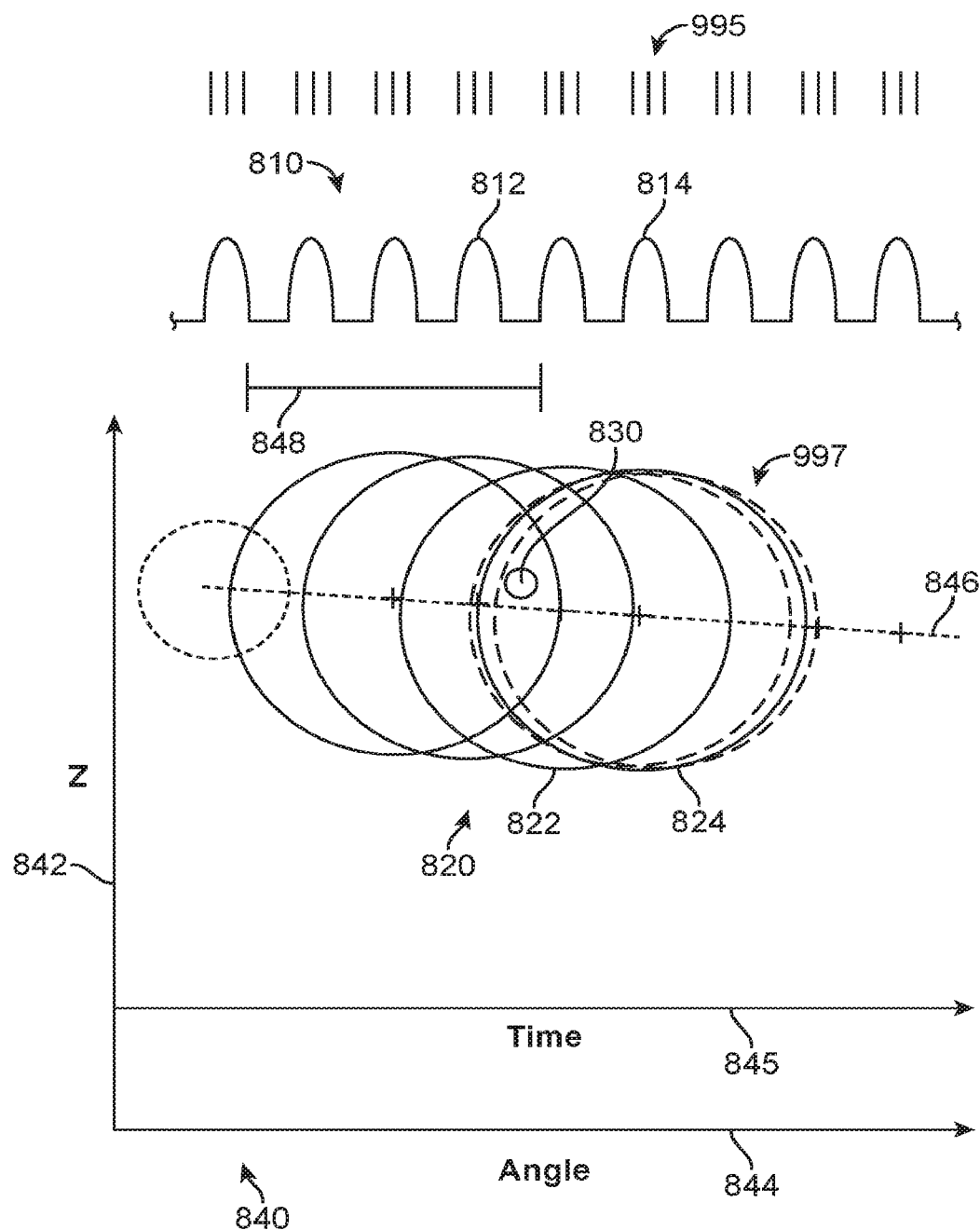
FIG. 5F shows a plurality of shedding pulses and sweeping of the ablative jet to provide smooth and controlled tissue erosion at a plurality of overlapping locations in accordance with embodiments.

FIG. 5F shows a plurality of shedding pulses 995 and sweeping of the ablative jet to provide smooth and controlled tissue erosion at a plurality of overlapping locations 997 in accordance with embodiments. This shedding frequency can be substantially faster than the pump frequency, when a pump is used, such that a plurality of shedding clouds are provided for each pulse of the pulsatile pump. The sweep rate of the probe can be related to shedding frequency to provide improved tissue removal, for example with the shedding clouds configured to provide overlapping pulses.

In many embodiments, the system comprises a pump having a frequency less than a frequency of the shedding pulses, in order to provide a plurality of shedding pulses for each pulse of the pump. The pump can have a pulse rate of at least about 50 Hz, for example within a range of about 50 Hz to about 200 Hz, and the shedding pulses comprise a frequency of at least about 500 Hz, for example within a range from about 1 kHz to about 10 kHz.

Although pulses of a pump are illustrated, similar scanning of pulsed clouds can be provided with a continuous flow pump.

While the nozzle can be configured in one or more of many ways, in many embodiments the nozzle comprises a Strouhal number (hereinafter "St") within a range from about 0.02 to about 0.3, for example within a range from about 0.10 to about 0.25, and in many embodiments within a range from about 0.14 to about 0.2.

In many embodiments, the Strouhal number is defined by:

$$St=(Fshed)*(W)/U$$

where Fshed is the shedding frequency, W is the width of the cavitating jet, and U is the velocity of the jet at the exit. A person of ordinary skill in the art can modify nozzles as described herein in order to obtain shedding frequencies suitable for combination in accordance with embodiments described herein, and experiments can be conducted to determine the cloud lengths and shedding frequencies suitable for tissue removal.

The nozzle configurations providing plurality of shedding clouds are suitable for use with one or more of the probes as described herein.

Referring again to FIG. 6C, based on the diagnostic results of the tissue of the organ to which the treatment apparatus 100 is delivered, the plurality of seeds 132 may have different dosages, distributions, and/or configurations so as to provide for localized targeted segmental treatment. For example, a treatment apparatus 100 with a greater distribution of radioactive seeds 132 on a first side than on a second side may be used to treat tissue in a target organ where diseased tissue is asymmetrically distributed.

Figure 9:
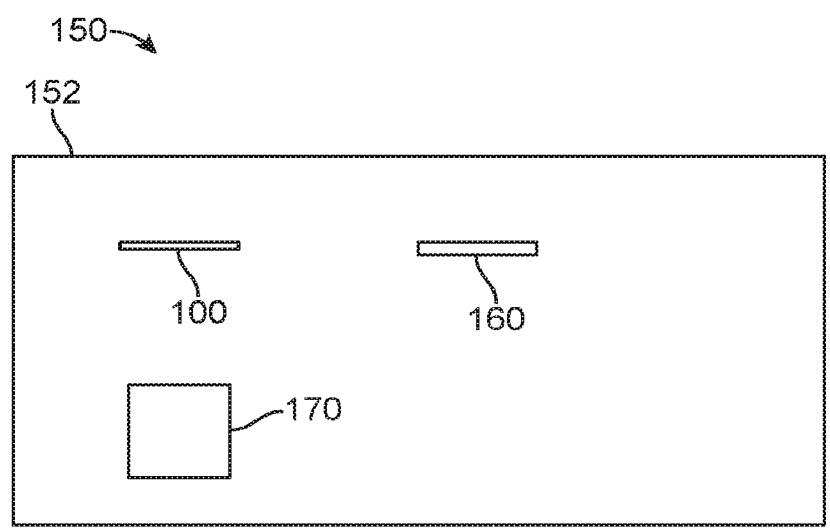
FIG. 9 shows a treatment apparatus in accordance with many embodiments.

FIG. 9 shows a treatment apparatus 150 in accordance with embodiments. The treatment apparatus 150 comprises an apparatus 100 as described herein comprising the radioactive substance 130. A second treatment apparatus 160 without the radioactive substance is provided. The second treatment apparatus 160 comprises structures similar to apparatus 100 but without the radioactive substance. The treatment apparatus 150 comprises a device 170 to test for the presence of cancer in a sample removed during surgery. The treatment apparatus 150 may comprise a kit 152 comprising the apparatus 100, the second apparatus 160 and the testing device 170. The kit 152 can be provided to the physician as a consumable or disposable kit, for example, comprising a sterile apparatus 100, a sterile apparatus 160 and device 170 which may or may not be sterile.

The second treatment apparatus 160, although referred to as the second treatment apparatus, can be provided independently and separately, for example. The apparatus 160 comprises many of the structures of the apparatus 100 as described herein. For example, the apparatus 160 may comprise the structures of apparatus 100 but without the radioactive substance.

The testing device 170 can be configured in one or more of many ways and may comprise one or more of many markers, such as antigen antibody combinations configured to detect biomarkers of one or more types of cancer. The treatment device 170 is configured to receive a sample from a surgical site of the patient as described herein and to process the surgical site material while the patient remains on the treatment support structure.

Figure 10:
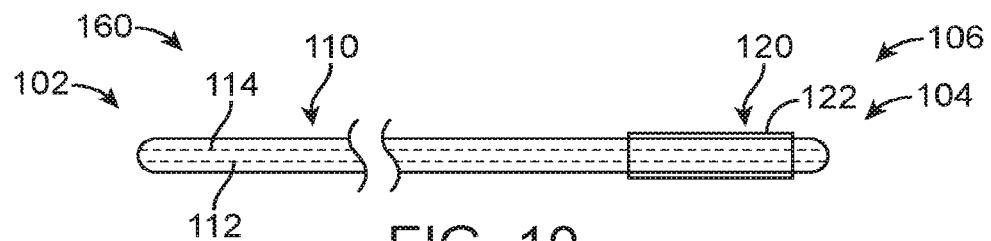
FIG. 10 shows apparatus in accordance with many embodiments.

FIG. 10 shows apparatus 160 in accordance with embodiments. Apparatus 160 comprises one or more of many structures similar to apparatus 100. However, apparatus 160 is provided without the radioactive substance 130 as described herein. Apparatus 160 is configured to expand from narrow profile configuration 106 to wide profile configuration 108, as described herein. Apparatus 160 can be left in the patient for a plurality of days similarly to apparatus 100. Apparatus 160 may comprise electrodes for electrocautery in the expanded profile configuration.

Figure 11:
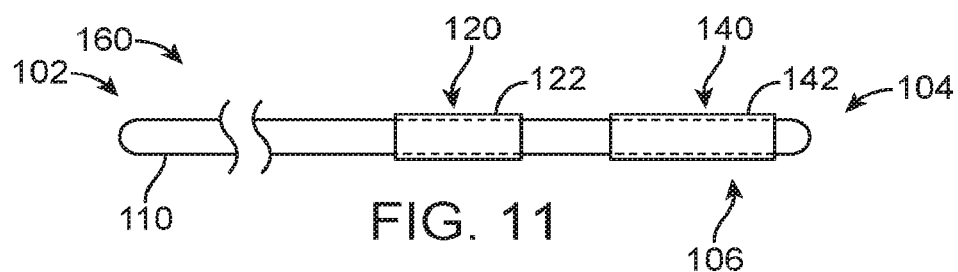
FIG. 11 shows apparatus comprising expandable support and anchor in accordance with many embodiments.

FIG. 11 shows apparatus 160 comprising expandable support 120 and anchor 140 as described herein. Apparatus 160 can be provided without the radioactive substance 130 as described herein. Apparatus 160 can be expanded from the narrow profile configuration 106 to the wide profile configuration 108 as described herein.

Apparatus 160 can be provided as an alternative to apparatus 100 as described herein, for example when the results of testing indicate that the patient does not have cancer. Expandable support of structure 120 can be injected with a non-radioactive substance such as saline, for example.

Alternatively or in combination, apparatus 160 can be injected with a radioactive substance to treat cancer with inflation of expandable support 120, for example, as shown in FIG. 10.

Figure 14A:
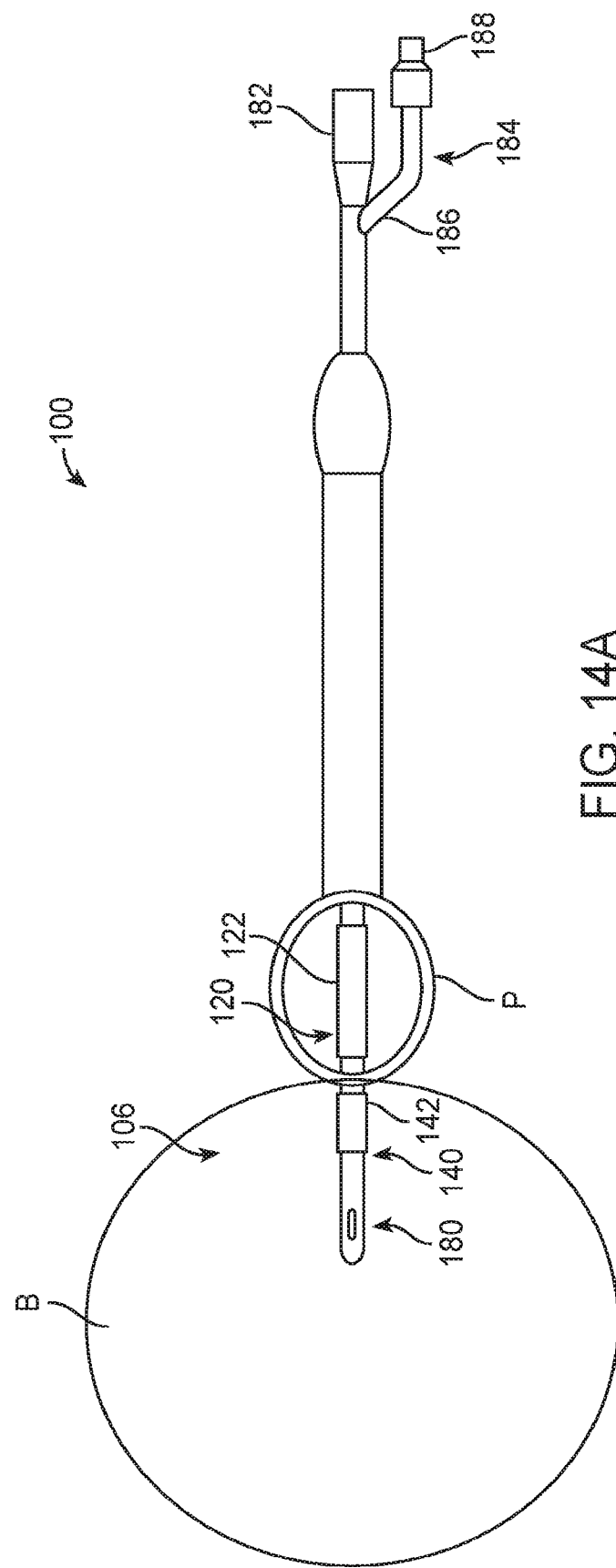
FIG. 14A shows a treatment apparatus comprising a bladder drain port, urine exit port, and inflation port in a narrow profile configuration in accordance with many embodiments.

FIG. 14A shows a treatment apparatus comprising a bladder drain port 180, urine exit port 182, and inflation port 184 in a narrow profile configuration 106 in accordance with many embodiments. In the narrow profile configuration, the anchor 140 can be advanced to the bladder neck of the patient and the expandable support 120 advanced to the resected prostate P. The bladder drain port 180 allows urine to flow out from the bladder B and exit the body through the urine exit port 182, via the y-connector 186. The y-connector 186 is also connected to the inflation port 184, which may comprise a Luer connector 188 that accepts a syringe to help inflate the anchor 140 and expandable support 120 simultaneously with saline.

Figure 14B:
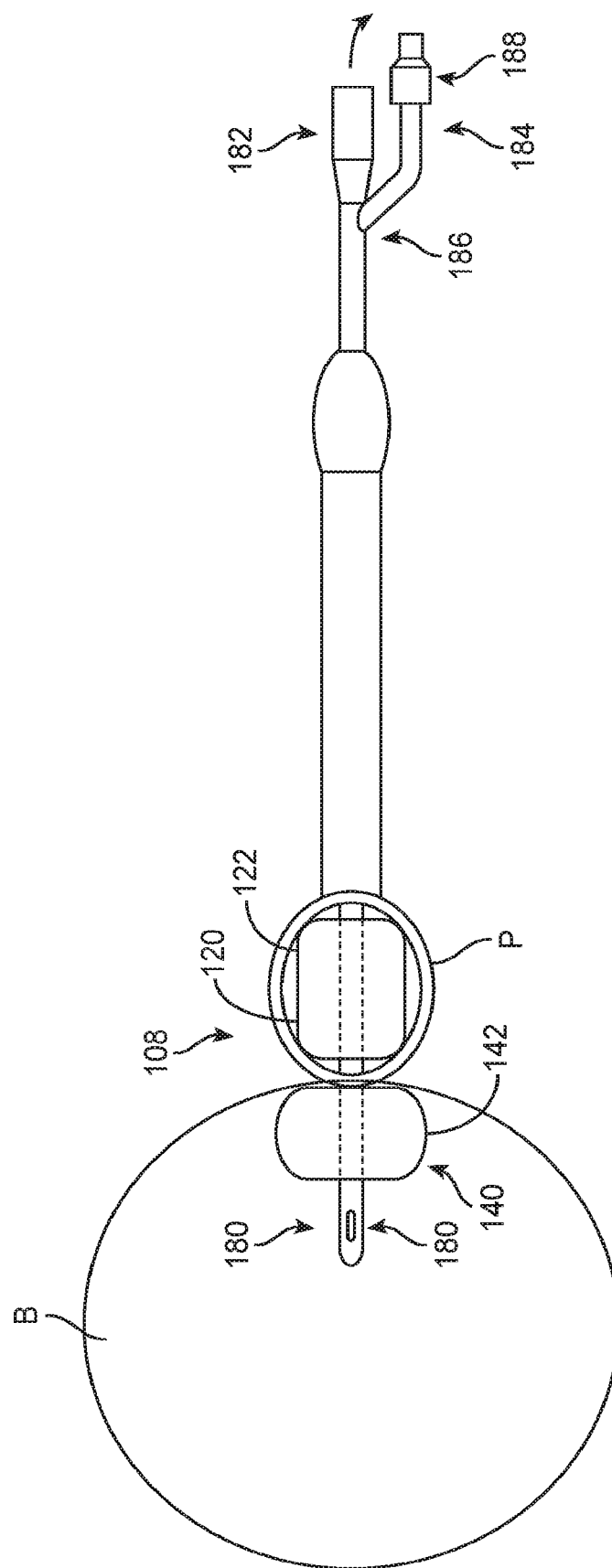
FIG. 14B shows apparatus in an expanded configuration in accordance with many embodiments.

FIG. 14B shows apparatus as in FIG. 14A in an expanded configuration 108 in accordance with many embodiments. The anchor 140 and expandable support 120 may be inflated via the injection of saline through the inflation port 184. In the expanded configuration 108, the movement of the anchor 140 and expandable support 120 is inhibited, and the apparatus can be left in the patient for a plurality of days, as described herein. When expanded, the anchor 140 is compressed against the bladder wall to help prevent the leak of urine from the bladder B to the prostate P.

Figure 15A:
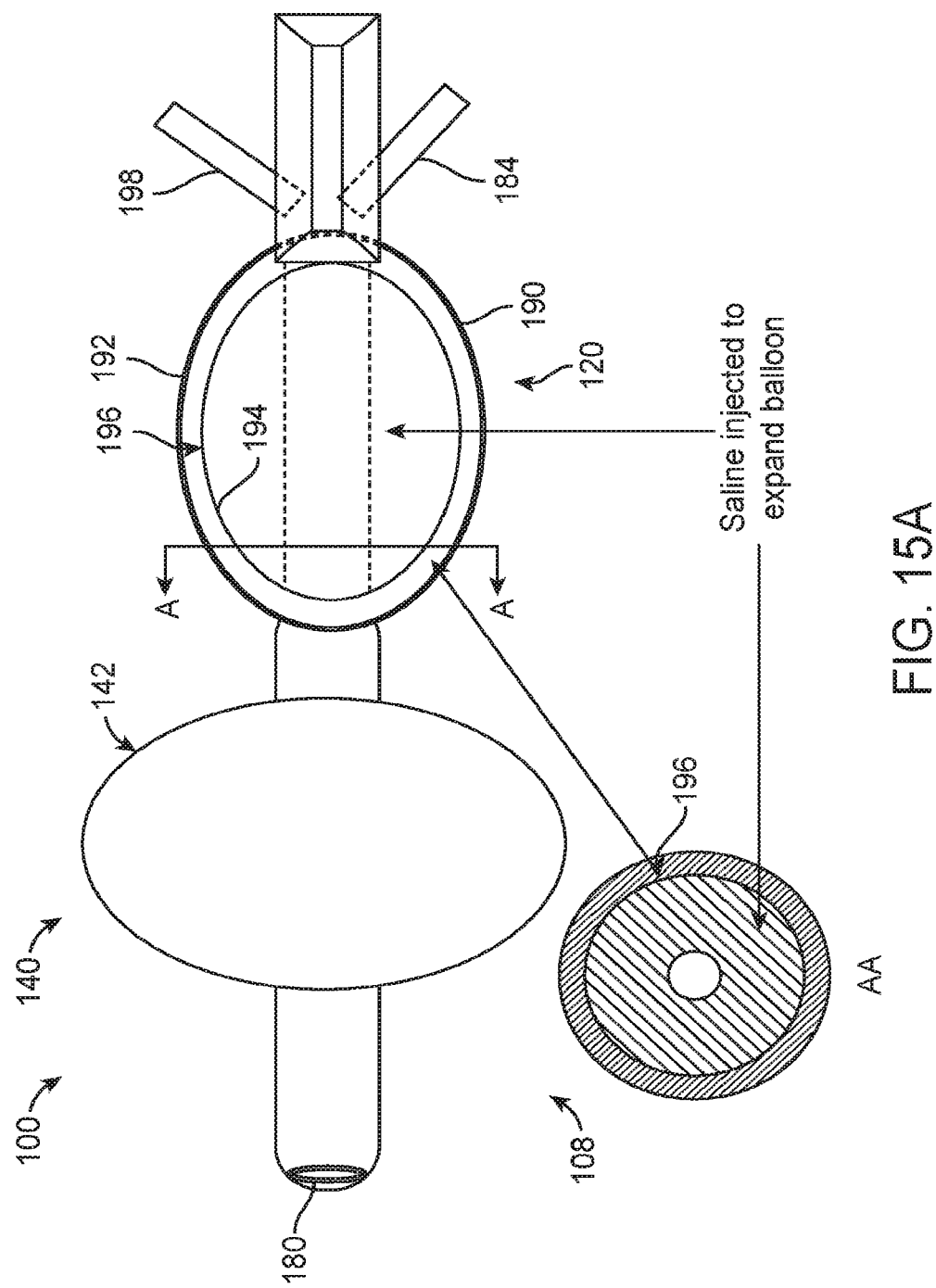
FIGS. 15A and 15B show a treatment apparatus comprising a sub-layer balloon and a treatment substance port in an expanded configuration in accordance with many embodiments.
Figure 15B:
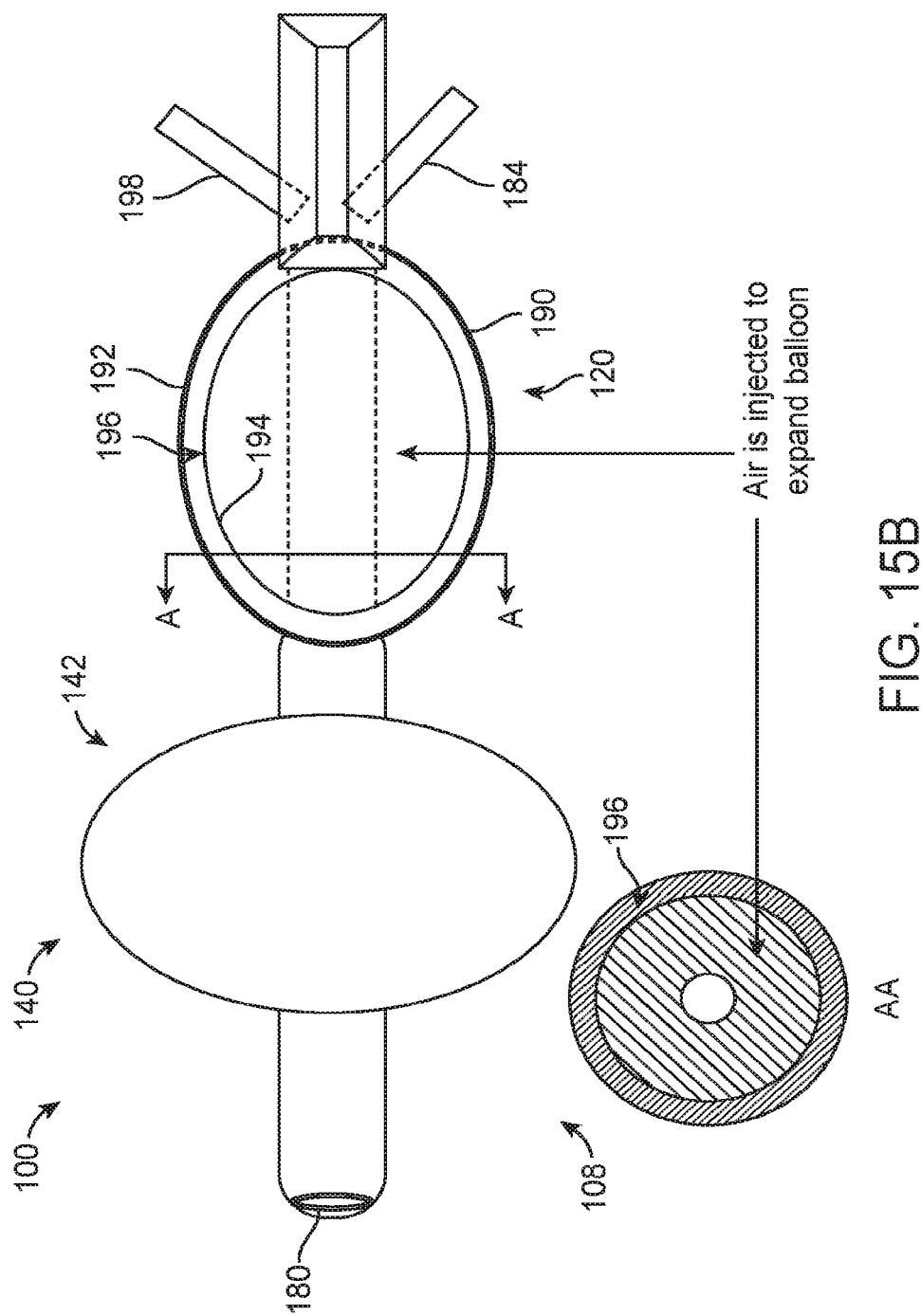

FIGS. 15A and 15B show a treatment apparatus 100 comprising a sub-layer balloon 190 and a treatment substance port 198 in an expanded configuration 108 in accordance with many embodiments. The sub-layer balloon 190 comprises an outer layer 192 and an inner layer 194, resulting in the creation of an inter-layer cavity 196. As shown in FIG. 15A, the inter-layer cavity 196 may be filled with radioactive or chemotherapeutic substances via injection of said substances into the treatment substance port 198. As shown in FIG. 15B, the inter-layer cavity 196 may be filled with air or other fluid (e.g., hot treatment fluid or steam) via injection of air or other fluid into the port 198. The inter-layer cavity 196 may be compartmentalized to allow for localized (non-uniform) diffusion across the layers 192, 194 as well. The outer layer 192 may be configured to inhibit dispersion of radioactive treatment substances across the surface of the sub-layer balloon 190. Alternatively or in combination, the outer layer 192 may be configured to allow dispersion of treatment substances across the surface of the sub-layer balloon 190. For example, the outer layer 192 may comprise a material that allows uniform diffusion of the treatment substance across the layer.

Figure 16:
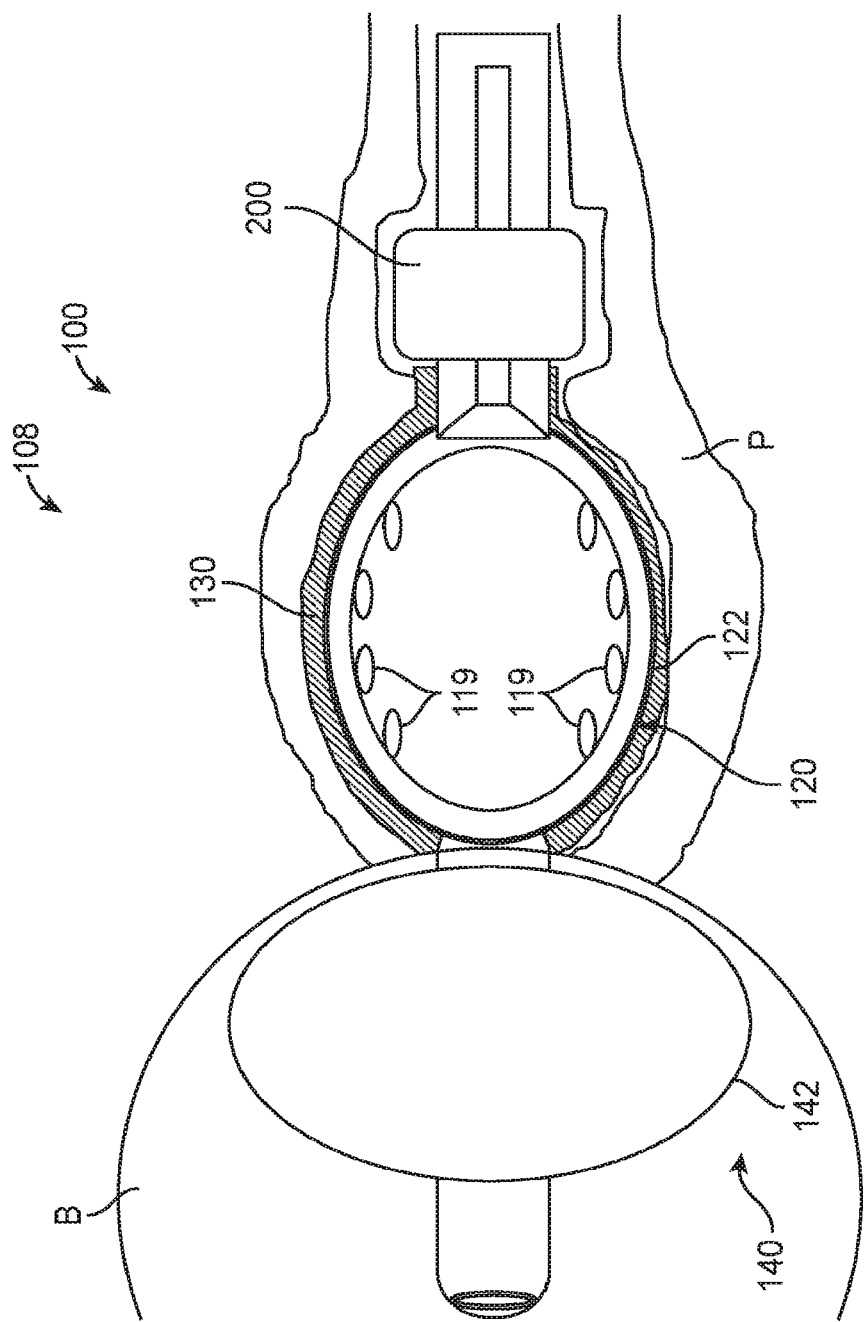
FIG. 16 shows a treatment apparatus comprising a peripheral isolation balloon in an expanded configuration in accordance with many embodiments.

FIG. 16 shows a treatment apparatus 100 comprising a peripheral isolation balloon 200 in an expanded configuration 108 in accordance with many embodiments. The expandable support 120 may comprise radioactive substances 130 and disperse said substances to the surrounding tissue as described herein. The peripheral isolation balloon 200 comprises an expandable structure positioned at the proximal end of the prostate P, and may be expanded simultaneously with the expansion of the anchor 140 and expandable support 120, for example. The expanded peripheral isolation balloon 200 can help prevent the radioactive substances from leaking into the urethra. Similarly, the expanded anchoring balloon 142 can help prevent the leak of radioactive substances into the bladder B. The use of either or both the anchoring balloon 142 and peripheral isolation balloon 200 can help improve the targeting of the treatment while limiting the exposure of the body to radioactive material. The treatment may be targeted to different locations of the prostate by choosing balloons 200 of the treatment apparatus 100 with varied permeability configurations or fenestration patterns.

FIGS. 17A1 and 17A2 show a treatment apparatus 100 comprising radioactive pellets 202 in accordance with many embodiments. The radioactive pellets 202 comprise a radioactive face 204 and a shielding face 206 that shields radioactivity from the radioactive face 204. The pellets 202 may further comprise a suture 208 that anchors the pellets to the expandable support 120, which is expanded as shown in FIG. 17A1, and/or to the elongate tubular member 110, as shown in FIG. 17A2. The radioactive side can be oriented toward the prostate capsule, and the shield side oriented away from the prostate tissue in order to shield tissue away from the prostate capsule.

Figure 17B:
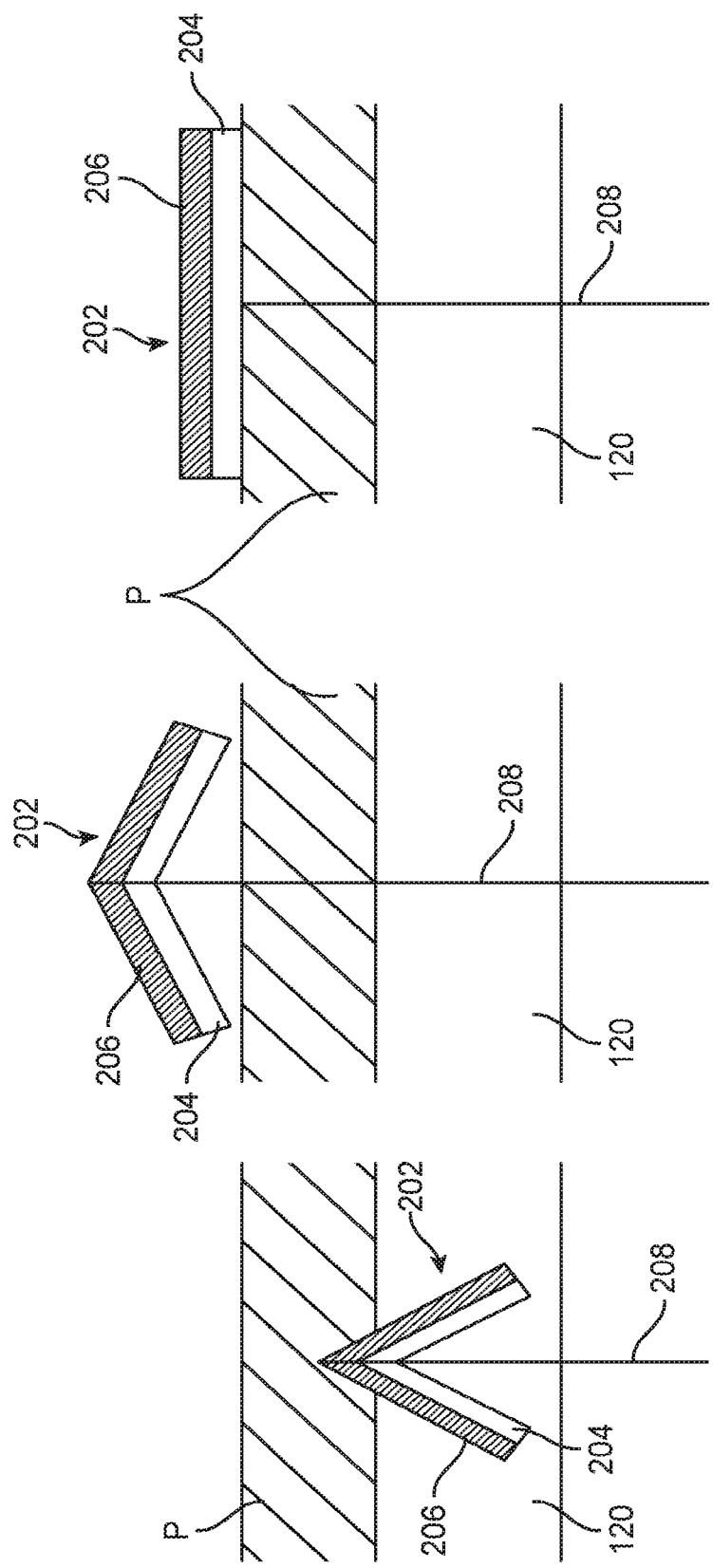
FIG. 17B shows the structure of radioactive pellets and method for configuration in accordance with many embodiments.

FIG. 17B shows the structure of radioactive pellets 202 and method for configuration in accordance with many embodiments. The pellets 202 are configured to be capable of penetrating tissue such as the prostate capsule P, and of expanding once on the outside of the tissue, so that the radioactive face 204 of the pellets can contact the outside of the tissue. For example, a pellet may be collapsed such that the shielding face 206 forms the exterior surface of the collapsed pellet; once the pellet has crossed the tissue, it can unfold such that the radioactive face 204 contacts the tissue. The pellets 202 may further comprise the suture 208 that allows the expanded pellet to the compressed inwards, so that the radioactive face 204 forms optimal contact with the tissue.

Figure 18:
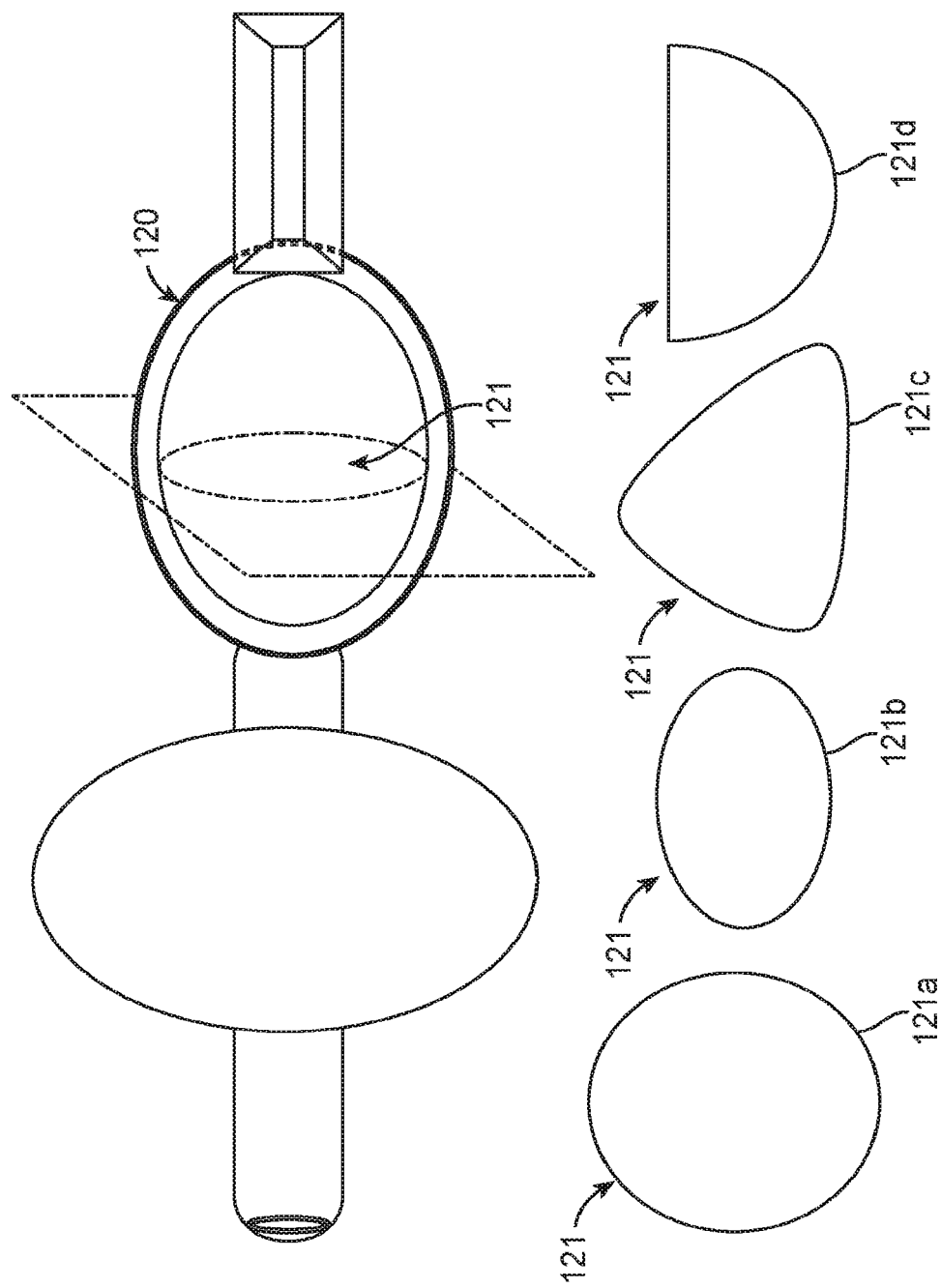
FIG. 18 shows an expandable support comprising a plurality of shapes in accordance with many embodiments.

FIG. 18 shows an expandable support 120 comprising one or more of a plurality of shapes in accordance with many embodiments. The expandable support can be shaped in one or more of many ways so as to conform to the profile of resected tissue. In many embodiments, the expandable support comprises a free standing profile corresponding to the shape of resected tissue. The support having free standing profile corresponding to the shape of the resected tissue can provide an improved fit to the tissue. The free standing profile may have a cross-sectional shape 121 comprising one or more of circular 121a, oval 121b, triangular 121c or semi-circular 121d, for example.

Figure 19:
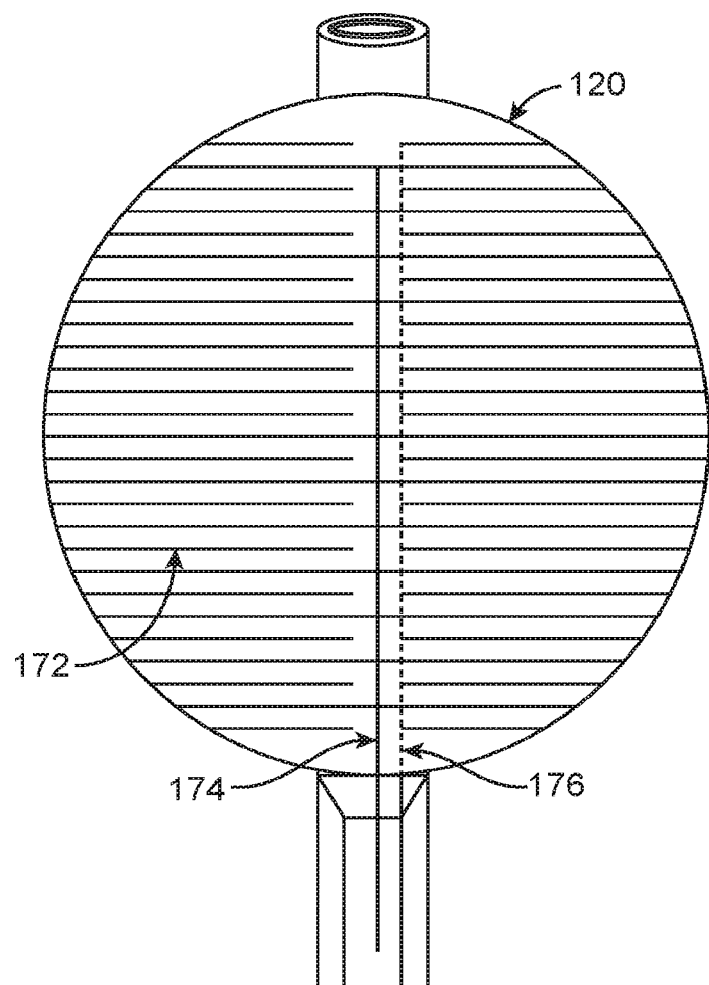
FIG. 19 shows bipolar cautery electrodes on an expandable support in accordance with many embodiments.

FIG. 19 shows bipolar cautery electrodes 172 on an expandable support 120 in accordance with many embodiments. The bipolar cautery electrodes can be located on the support in one or more of many ways. For example, the active electrode 174 can be located on an outer surface of the expandable support and the return electrode 176 located on an inner surface of the expandable support. Alternatively or in combination, both the active electrode and the return electrode may be connected to the active line so that the expandable support may be changeable to a mono-polar configuration. In many embodiments, the bipolar electrodes comprise a plurality of active electrode branches and a plurality of return electrode branches, in which the active electrode branches are substantially interleaved with the return electrode branches.

The expandable support may comprise a balloon wall comprising one or more of a high-temperature resistant elastomeric material.

The embodiments of FIG. 19 may comprise one or more structures of the bipolar electrodes on the support of the embodiments shown in FIG. 12 as described herein, and vice versa.

Figure 20:
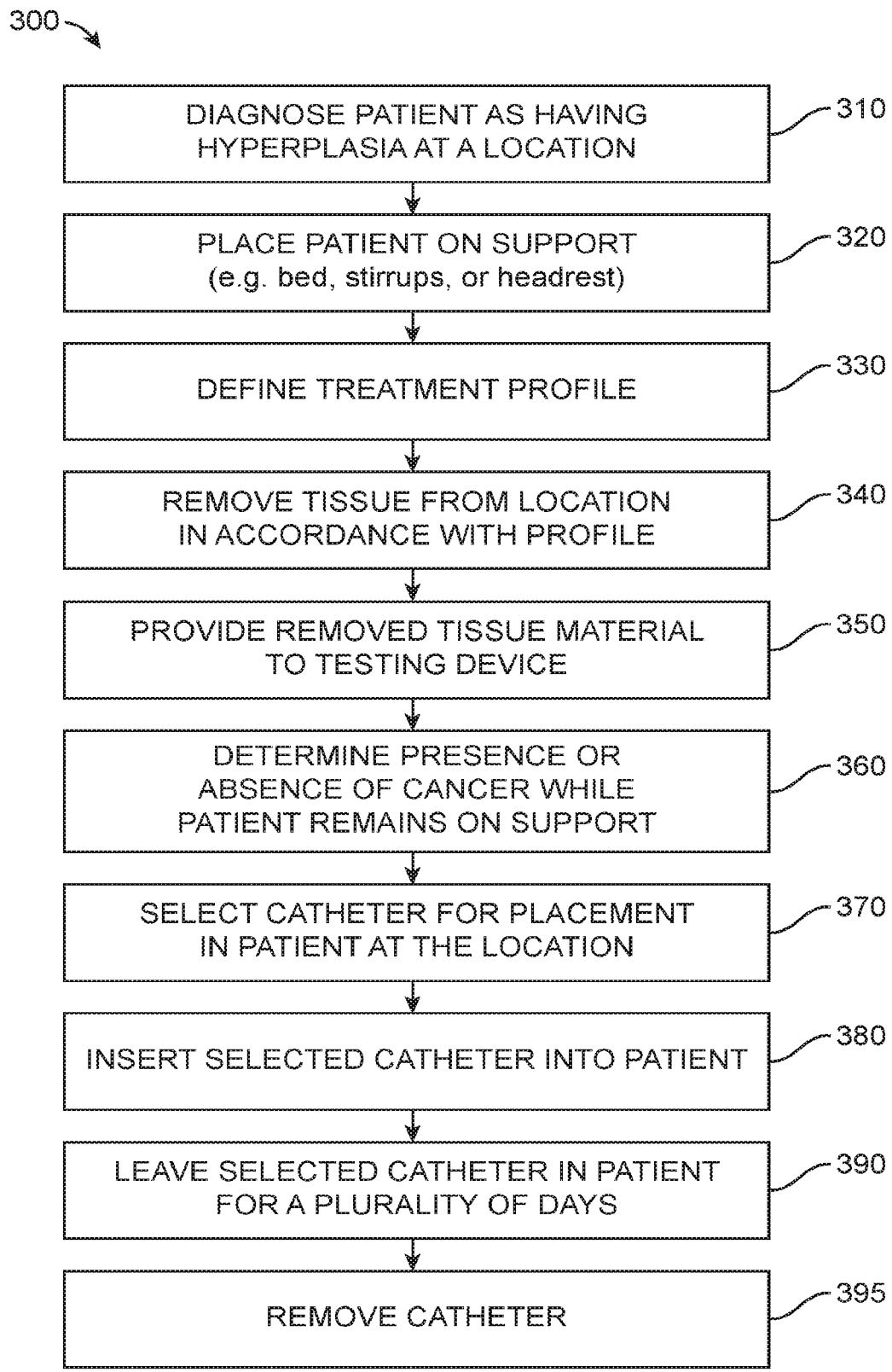
FIG. 20 shows a method of treating a patient in accordance with many embodiments.

FIG. 20 shows a method 300 of treating a patient in accordance with embodiments. At a step 310 the patient is diagnosed with having hyperplasia at a location. The hyperplasia may comprise benign hyperplasia, such as benign prostate hyperplasia (BPH); alternatively, the hyperplasia may comprise a cancerous hyperplasia. In many embodiments the patient is diagnosed as having the hyperplasia and subjected to additional testing. The location of the patient where the hyperplasia is located may comprise a location of an organ, such as the prostate, the eye, the kidneys, or any other known organs, for example, the breast.

The patient is placed on a support at a step 320. The support can be one or more of many objects that supports the patient. For example, a bed, stirrups, a chin rest or a head rest, for example. At a step 330 a treatment profile is defined. The treatment profile can be defined in one or more of many ways, and this step is optional. The treatment profile may comprise an image guided treatment profile to remove a pre-defined amount of tissue from the organ in order to substantially remove the hyperplasic tissue. The treatment profile can be defined for removal of material from inside the organ outwardly toward a capsule of the organ, for example.

At a step 340 tissue is removed from the location in accordance with the profile. The tissue can be removed in one or more of many ways. For example, with mechanical scraping, abrading, a water jet, laser ablation, radio frequency ablation, erosion with chemical processes in combinations thereof for example. In many embodiments the tissue is removed without a predefined profile. For example, with visual observation of the organ and removal of the tissue.

At a step 350 the removed tissue material is provided to a testing device. The testing device may comprise one or more of many devices as disclosed herein.

At a step 360 the presence or absence of cancer is determined while the patient remains on the support. This has the advantage of allowing the treatment to be determined while the patient is in surgery and while access to the surgical site is available.

At a step 370 a catheter is selected for placement in the patient at the location. The catheter may comprise the elongate tubular member and support structure as described herein. For example, the selected catheter may comprise the catheter having the radioactive substance or the catheter without the radioactive substance.

At a step 380 the selected catheter is inserted into the patient. The selected catheter can be inserted with the narrow profile configuration as described herein and expanded to the wide profile configuration as described herein in order to engage tissue at the surgical site with the expandable support.

At a step 390 the selected catheter remains in the patient for a plurality of days. The plurality of days may comprise a pre-determined number of days in accordance with a treatment plan. For example, the plurality of days may comprise a plurality of days to deliver a radiation therapy with a radioactive substance as described herein. Alternatively the plurality of days may comprise of a plurality of days determined for a treatment catheter placed without a radioactive substance as described herein.

At a step 395 the catheter is removed.

Although the above steps show method 300 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 300 may be performed with the circuitry as described herein, for example one or more of the processor or logic circuitry such as the programmable array logic for field programmable gate array. The circuitry may be programmed to provide one or more of the steps of method 600, and the program may comprise program instructions stored on a computer readable memory or programmed steps of the logic circuitry such as the programmable array logic or the field programmable gate array, for example.

Diagnostic Test Apparatus

The diagnostic test apparatus 170 may comprise one or more of many known or commercially available tests. In many embodiments, the one or more tumor markers comprise one or more tumor markers found on the cancer itself, for example with the tissue collected from the surgical procedure. The apparatus may comprise multiplexing instruments. The apparatus 170 may comprise one or more commercially available components such as LabMAP components commercially available from Luminex (www.millipore.com) or Environic ChemPro 100 eNose, which can examine and discriminate prostate cancer by analysis of urine headspace. Instead of urine, the apparatus 170 may be exposed to resected aspirate fluid (non-contact) in a chamber that would allow for detection via air. The apparatus 170 may comprise components to test for one or more of the following markers:

Adipokines
TNF-RI
TNF-RII
Leptin
TNFa
VEGF
Adiponectin
Resistin
Immune Response
IL-2R
sIL-6R
MIF
IL
IL-6
G-CSF
IL-1Ra
MPO
MIP-1
MCP-1a
sE-Selectin
IP-10
Metalloproteinases
MMP-2
MMP-3
MMP-9
PAI-1 (active)
tPAI-1
Adhesion
SVCAM-1
SICAM-1
Hormones, Growth Factors
FSH
LH
Prolactin
TSH Adrenocorticorticotropic hormone
GH
IGFBP-1
Tumor Markers
HCG
AFP
aKallikrein_10
Carcinoembryonic antigen
CA-125
CA 15-3
CA 19-9
CA 72_4
Kallikrein_8
Mesothelin
Growth and Tumor Markers
EGFR
EGF
TGFa
HGF
NGF
ErbB2
Other
FAS_L
Fractalkine
EOTAXIN
Cytokeratin_19
Fas Components for testing such markers are commercially available as described in "Assessment of 54 Biomarkers for Biopsy-Detectable Prostate Cancer", Parekh et al., Cancer Epidemiology Biomarkers and Prevention.

The treatment apparatus 100 described herein may be used to detect and localize cancer in real-time. The treatment apparatus 100 may be used in combination with the diagnostic test apparatus 170 to detect and localize cancer in real time. The cancer can be identified when the patient remains on the support, and suitable treatment determined for example. The diagnostic testing and corresponding identification of the cancer can be real time, or within about 5 minutes, for example.

Figure 21C:
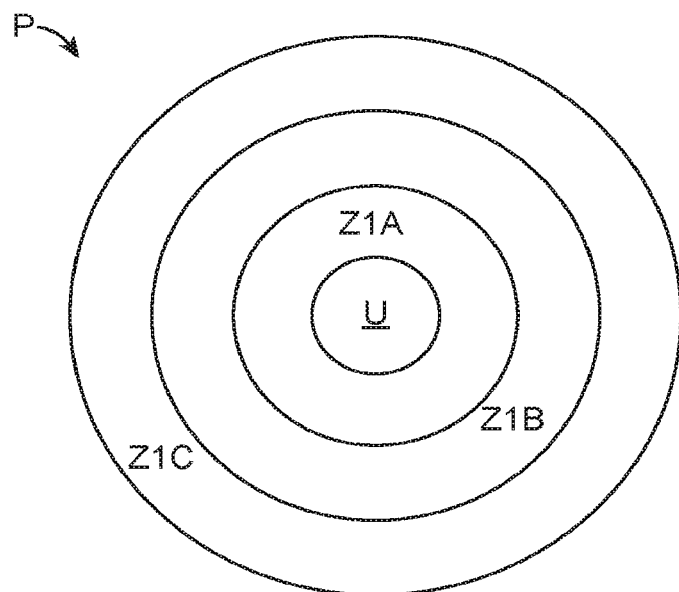
FIGS. 21C and 21D show transverse views of the prostate divided into tissue collection zones.

FIG. 21A shows the treatment apparatus 100 placed in the urethra U of a patient to reach the bladder. The treatment apparatus 100 may be threaded along or through a handpiece 210 which may comprise a plurality of aspiration ports 220 distributed along the length of the distal portion of the handpiece 210. As shown in FIGS. 21A and 21B, the treatment apparatus 100 may be retracted proximally in the direction indicated by arrow 201 (e.g., the distal tip of the treatment apparatus 100 may be retracted from the bladder toward the penis) to remove tissue from the base of the prostate P to the apex of the prostate such as with a liquid jet 101. As tissue is removed, the resected tissue may be suctioned through the aspiration ports 210.

The prostate P may be divided into cutting zones Z1, Z2, Z3, Z4, Z5, Z6, and Z7, for example. The zones Z1, Z2, Z3, Z4, Z5, Z6, and Z7 may be sagittal zones and the treatment apparatus 100 (and the liquid jet 101) may be fully rotated as the apparatus 100 is retracted. The zones Z1, Z2, Z3, Z4, Z5, Z6, and Z7 may be transverse zones and the treatment apparatus 100 (and the liquid jet 101) may be partially rotated as the apparatus 100 is retracted. As the treatment apparatus 100 begins to cut in zone Z1 toward Z2, the aspirate may be analyzed in real-time in zone Z1 to determine the presence of cancer. The analysis can continue in zone Z2, Z3, and so on so as to locate the source(s) of cancer within the prostate.

The presence of cancerous cells can be detected in many ways. Optical absorption and scattering may be used to detect higher blood concentration and lower oxygen level characteristics of cancerous cells. Fluorescence spectroscopy may be used to detect the different molecular composition of cancerous cells or even pre-cancerous cells. Optical coherence domain reflectometry may be used to detect structural changes and patterns in cellular architecture which may be characteristic of cancerous cells. Fluorescence microscopy may also be used to image resected tissue sections to visualize and semi-quantitatively analyze the distribution of cancerous cells. For example, resected tissue sections may be treated with a photodynamic agent known to accumulate in tumor tissue, such as 5-aminolevulinic acid (5-ALA). 5-ALA can induce protoporphyrin IX (PPIX), which fluoresces in tissue and can thus be visualized via fluorescence microscopy. Fluorescence images may be digitized and their fluorescence intensity quantified, in order to semi-quantitatively analyze the distribution of cancerous cells. These detection methodologies are examples only and may be used alone, in combination with one another, or in combination with further cancer cell detection methodologies. An example of cancer diagnosis using light scatter is described in "Early diagnosis of cancer using light scatter spectroscopy," Backman, V., Massachusetts Institute of Technology, 2001.

Figure 21D:
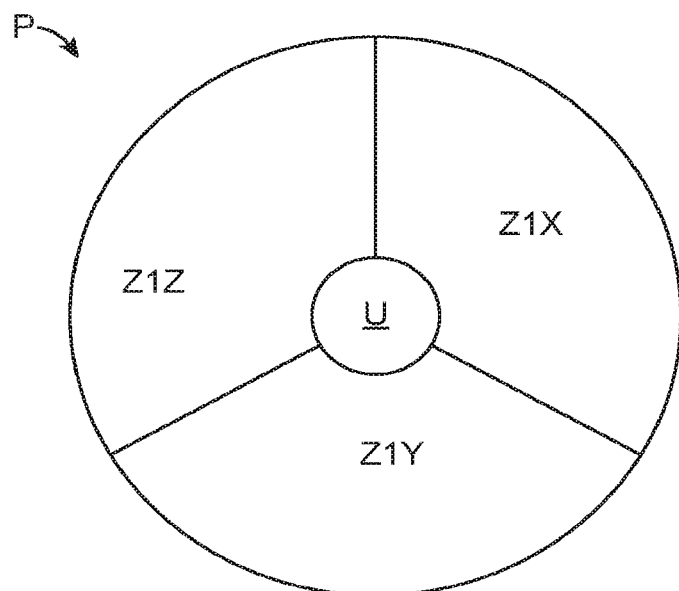

The division of the prostate P into 7 cutting zones is for example only. Different numbers of divisions of the prostate P may be used. For example, a zone Z1 may be divided into two or more zones based on the depth of the tissue in relation to the apparatus 100 (see zones Z1A, Z1B, and Z1C shown in FIG. 21C) and/or or based on radial location (see zones Z1X, Z1Y, and Z1Z shown in FIG. 21D).

By identifying the location of the cancer within the prostate P, therapy may be targeted rather than homogenous. Homogenous treatment may result in excess and unwanted collateral damage to neighboring tissues, vessels, nerve, as well as remaining non-cancerous prostatic tissue. The treatment may be adapted and dosed to reflect the severity of cancer between the different zones of the prostate P. Cancer treatment dosage can be determined real-time base on the real-time diagnostic testing described above. Dosage may be adjusted based on degree/state of cancer for entire prostate or may be adjusted for each prostate zone as illustrated in FIGS. 21A to 21D. The prostate may be diagnosed and treated in segments. As described herein, the apparatus 100 may be provided with balloon(s) and/or seeds which may allow for targeted segmental treatment.

As disclosed herein, the apparatus may comprise multiplexing instruments. The apparatus 170 may comprise one or more commercially available components such as Lab-MAP components commercially available from Luminex (www.millipore.com) or Environic ChemPro 100 eNose, which can examine and discriminate prostate cancer by analysis of urine headspace. Instead of urine, the apparatus 170 may be exposed to resected aspirate fluid (non-contact) in a chamber that would allow for detection via air.

EXPERIMENTAL

Figure 22:
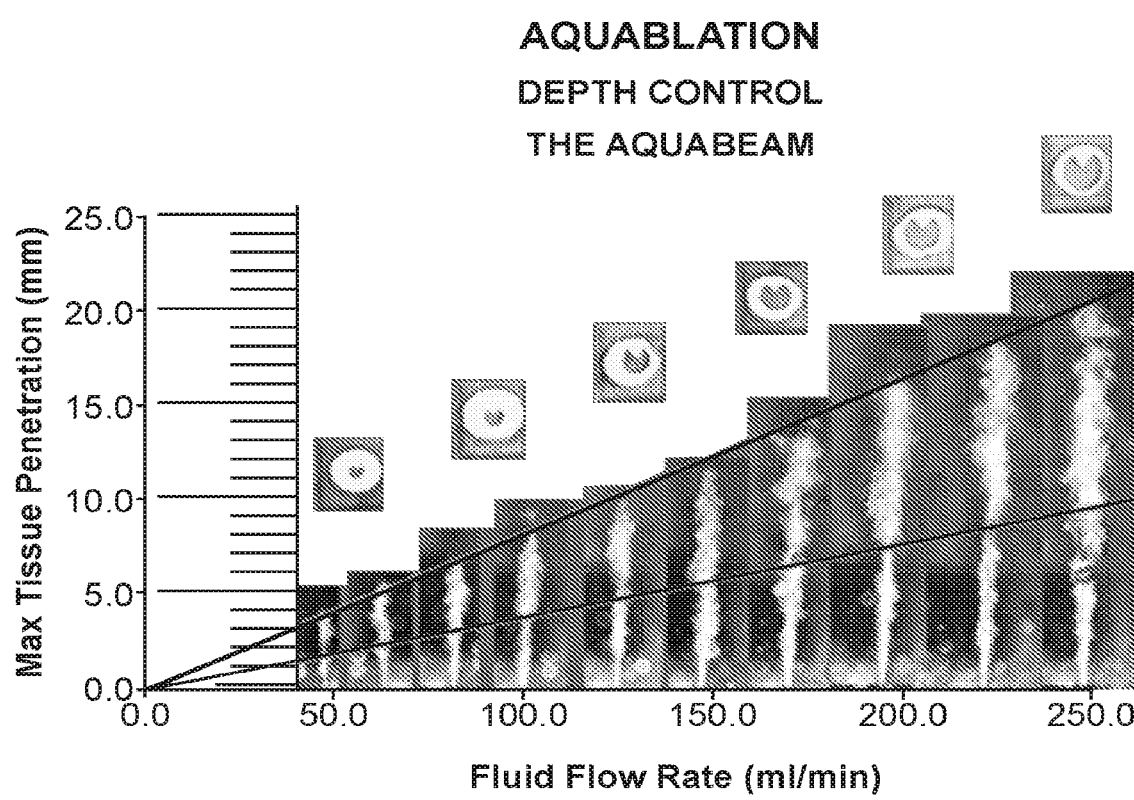
FIG. 22 shows maximum tissue penetration depth of cutting and flow rate through a nozzle in accordance with embodiments.

FIG. 22 shows maximum tissue penetration depth of cutting and flow rate through a nozzle in accordance with embodiments. The maximum penetration depth corresponds substantially to the length of the cavitation bubbles of the jet comprising the "cold" aquablation flame. The maximum tissue penetration depth of ablation corresponds directly to the flow rate and in many embodiments is linearly related to the flow rate.

The inset of FIG. 22 shows cut potato as a model of prostate BPH, in accordance with embodiments. The maximum penetration depth of potato corresponds closely to the maximum cut depth of BPH. The potato is shown cut with 10 different flow settings corresponding to rates within a range from about 50 ml/min to about 250 ml/min with a nozzle and rotating probe as described herein. The maximum penetration depth ranges from about 4 mm at 50 ml/min to about 20 mm at about 250 ml/min.

In many embodiments, the cavitation cloud growth and length comprises a function of flow rate, which is proportional to the injection pressure and vice versa, for an appropriately configured nozzle as described herein. As the pressure increases, the maximum erosive radius appears to increase linearly, which is shown as the maximum penetration depth of FIG. 22.

High velocity cavitating jets can be created by using an known high pressure pump to force the water through a nozzle in either a continuous or pulsatile flow. Despite the flow type produced by a pump, the cavitation phenomenon will be pulsatile due to the unsteady nature of vapor cavities and the cavity formation will be pulsatile even in a continuous flow jet as described herein. Without being bound to a particular theory, it is believed that both pulsatile and continuous flow waterjets will result in equivalent amounts of material erosion over a given amount of time. In many embodiments, nozzle geometry is configured to provide the flow dynamics and cavitation process as described herein. In many embodiments, the nozzle is configured to inhibit tight constriction at the waterjet exit, which can be related cavitation can occur inside the nozzle itself. In many embodiments, the sharp corners cause the water to separate from the wall and converge towards the nozzle centerline, further constricting the waterjet pathway while simultaneously reducing frictional effects caused by the nozzle wall. This results in an increased velocity along with the corresponding pressure drop and the vapor cavities formation. Vapor cavity formation will impact the overall flow dynamics as their eventual collapse results in turbulence and can affect erosion depth. A person of ordinary skill in the art can conduct experiments to determine appropriate nozzle geometry and flow rate to provide tissue removal as described herein without undue experimentation.

Aquablation

Submerged waterjet cutting as described herein has the capability to take advantage of the cavitation phenomenon to treat patients with Benign Prostatic Hyperplasia (BPH). The jet removes the excess soft tissue growth seen in BPH through the pressure pulses and microjets caused by collapsed vapor cavities. The waterjet direction can be manipulated by changing the location and orientation of the devices nozzle, either by translating the nozzle along the anterior-posterior direction or by rotating the nozzle up to 180 degrees, for example.

As vapor cavity formation and its erosive strength is a function of both injection pressure and the flow dynamics, the depth of material can be controlled by configuring the pressure as well as nozzle geometry. A greater injection pressure will result in a faster exit velocity. As discussed herein, the nozzle geometry can further increase the velocity depending on the constriction and will affect the degree of pressure drop as the waterjet exits through the Venturi effect. These factors can result in longer distances the cavitation clouds can grow to and travel before collapsing and releasing pressure pulses and microjets. The nozzle geometry and pressure settings of the Aquablation system have been optimized to give the user precise control and ensure the cavitating jet removes only the desired benign tissue growth.

The images provided herein show the how tissue erosion depth is a function of pressure, in accordance with embodiments. The images show the smaller cavitation cloud length and corresponding tissue resection depth for a lower injection pressure as compared with other images.

In many embodiments, Aquablation as described herein is capable of removing the excess tissue growth, e.g. BPH, with inhibited removal and damage of arteries and veins. The pressure pulses and microjets caused by cavitation exceed the threshold energy required to erode the soft tissue growth, and may cause minimal damage to other structures like vessels which have a much higher threshold energy. Repeated and concentrated pressure pulses and microjets may cause fatigue stress on the vasculature and result in bleeding, but the Aquablation system algorithm and treatment instructions as described herein are configured designed to inhibit such damage.

In many embodiments, generation of harmful emboli are inhibited. Vapor cavity formation may benefit from a minute nucleus of air already present in the blood stream, for example. Cavitation can result in the growth of the nucleus without any additional air being introduced into the system. Furthermore, the cavity will collapse once the local jet pressure exceeds the vapor pressure, such that the air pockets may reduce back to their original nucleus size. In many embodiments, embolus formation is inhibited as cavitation depends on and can be limited to micro amounts of air native to the saline solution surrounding the urethra, and the vapor cavities quickly dissipate as the jet pressure begins to rise.

Aquablation as described herein takes advantage of this phenomenon. The naturally self-limiting erosive radius and unique ability to precisely ablate tissue with a low damage threshold energy while minimizing damage to nearby structures with a more dense cellular structure, such as arteries, make Aquablation as described herein a useful surgical tool for treating BPH. Coupled with the nearly isothermal property of cavitation as described herein, which can mitigate collateral damage and provide improved healing and an improved safety profile.

Figure 23:
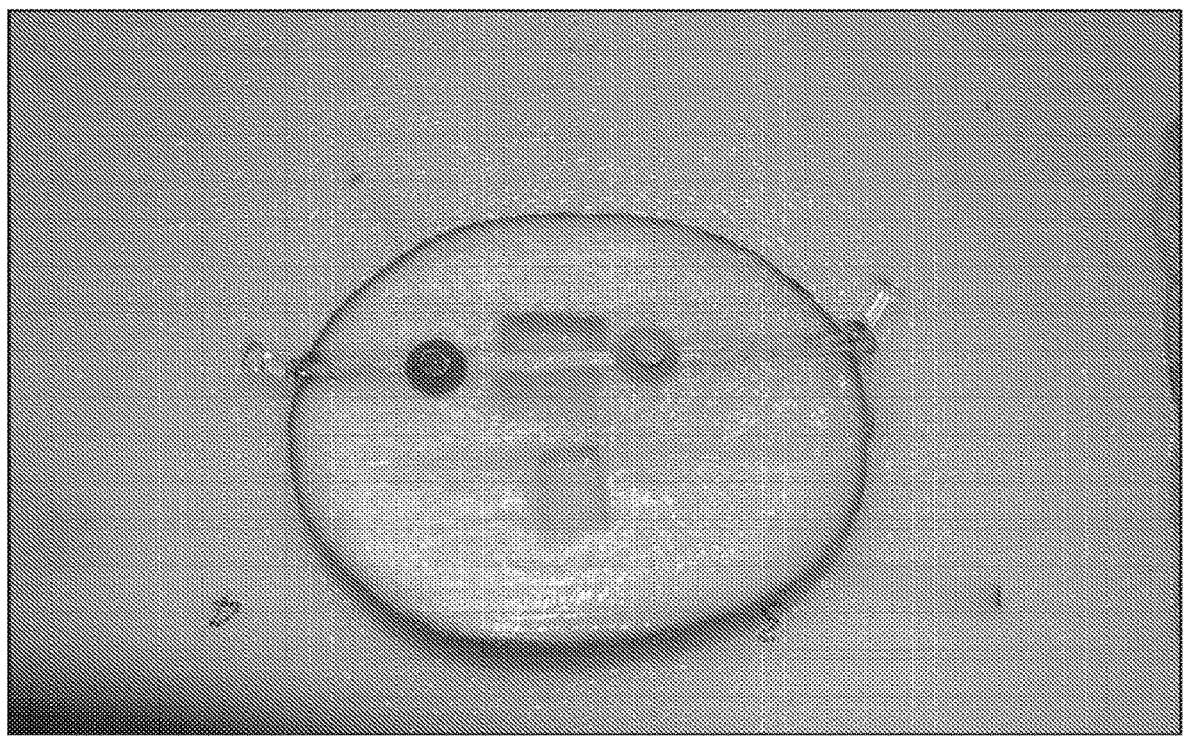
FIG. 23 shows selective removal of potato with a porcine blood vessel positioned over the incision of the potato as a model for selective removal of tissue.

FIG. 23 shows selective removal of potato with a porcine blood vessel positioned over the incision of the potato as a model for selective removal of tissue. The porcine blood vessel was placed on the potato prior to the incision, such that the porcine blood vessel was exposed to the water jet with cavitation in order to remove the potato. Aquablation resected the soft potato tissue model, which is a close proxy for the benign tissue growth seen in BPH, without causing severe damage to the porcine vessel.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A method of treating a patient, the method comprising:
   placing the patient on a support;

removing a sample of a tissue from the patient using a water jet source while the patient is on the support;

placing, while the patient is on the support, a first catheter or a second catheter in the patient subsequent to removing the sample, the first catheter comprising a radioactive substance to treat a cancer of the patient subsequent to surgery, the second catheter without the radioactive substance for cancer treatment; and receiving the sample using a device; and determining using the device, while the patient is on the support, whether the patient has the cancer in order to select the first catheter or the second catheter for placement in the patient.

2. The method of claim 1, comprising: using the first catheter comprising the radioactive substance to treat the cancer of the patient subsequent to surgery.

3. The method of claim 1, comprising: using the second catheter without the radioactive substance to treat the patient subsequent to surgery.

4. The method of claim 1, comprising: determining a presence of the cancer in each of a plurality of zones of a prostate, in order to select the first catheter or the second catheter for placement into said each of the plurality of zones of the prostate.

5. The method of claim 1, wherein the selected first or second catheter is configured to be inserted into the patient's body with a narrow profile configuration and to expand to a wide profile configuration to engage tissue at a surgical site of the patient.

6. The method of claim 1, wherein the selected first or second catheter is configured to remain in the patient's body for a predetermined number of days.

7. The method of claim 1, wherein the selected first catheter is configured to be inserted into the patient's body with a narrow profile configuration and to expand to a wide profile configuration to place the first catheter against tissue within the patient's body to treat the tissue within the patient's body with the radioactive substance.

8. The method of claim 1, wherein the selected second catheter is configured to be inserted into the patient's body with a narrow profile configuration and to expand to a wide profile configuration to place the second catheter against tissue within the patient's body to treat the tissue within the patient's body without the radioactive substance.

9. The method of claim 1, wherein the first catheter comprises a first elongate tubular member and a first expandable support for insertion into the patient and the second catheter comprises a second elongate tubular member and a second expandable support.

10. The method of claim 1, wherein, the first catheter or the second catheter is placed in the patient with the patient on the support.

11. The method of claim 1, wherein the determining whether the patient has cancer comprises one or more of testing for optical absorption and scattering on the tissue, performing fluorescence spectroscopy on the tissue, or performing optical coherence domain reflectometry on the tissue.

12. The method of claim 1, wherein determining whether the patient has cancer comprises determining whether the tissue comprises cancer tissue in real-time concurrently with removing the tissue.

13. The method of claim 1, wherein determining whether the patient has cancer further comprises determining whether the tissue comprises pre-cancerous tissue.

* * * * *